(12) United States Patent
Shin et al.

(10) Patent No.: US 11,999,768 B2
(45) Date of Patent: Jun. 4, 2024

(54) MUTANT URACIL DNA GLYCOSYLASE WITH IMPROVED THERMAL SENSITIVITY

(71) Applicants: ENZYNOMICS CO. LTD., Daejeon (KR); DAEGU GYEONGBUK INSTITUTE OF SCIENCE AND TECHNOLOGY, Daegu (KR)

(72) Inventors: Yong Keol Shin, Daejeon (KR); Jeongyeon Yoon, Daejeon (KR); Ki Hoon Nam, Daejeon (KR); Seulki Lim, Daejeon (KR); Wookyung Yu, Daegu (KR); Seongjun Park, Gyeongsangnam-do (KR); Juhwan Lee, Daegu (KR); Sangyeol Kim, Gyeongsangnam-do (KR); Moo Seok Kang, Busan (KR); Minjae Seo, Daegu (KR)

(73) Assignees: Enzynomics Co. Ltd., Daejeon (KR); Daegu Gyeongbuk Institute of Science and Technology, Daegu (KR)

( * ) Notice: Subject to any disclaimer, the term of this patent is extended or adjusted under 35 U.S.C. 154(b) by 704 days.

(21) Appl. No.: 17/264,509

(22) PCT Filed: Oct. 22, 2020

(86) PCT No.: PCT/KR2020/014468
§ 371 (c)(1),
(2) Date: Jan. 29, 2021

(87) PCT Pub. No.: WO2022/085818
PCT Pub. Date: Apr. 28, 2022

(65) Prior Publication Data
US 2022/0396602 A1    Dec. 15, 2022

(51) Int. Cl.
| | | |
|---|---|---|
| C07K 14/245 | (2006.01) | |
| C12N 15/63 | (2006.01) | |
| C12Q 1/6848 | (2018.01) | |
| C12Q 1/686 | (2018.01) | |

(52) U.S. Cl.
CPC ............ *C07K 14/245* (2013.01); *C12N 15/63* (2013.01); *C12Q 1/6848* (2013.01); *C12Q 1/686* (2013.01)

(58) Field of Classification Search
None
See application file for complete search history.

(56) References Cited

PUBLICATIONS

Pearl et al., Mutation Res., 460:165-181 (2000) (Year: 2000).*
Cai et al., Cell Mol. Life Sci., 70:3145-3156 (2013) (Year: 2013).*
(Continued)

*Primary Examiner* — Thomas J. Visone
(74) *Attorney, Agent, or Firm* — Vorys, Sater, Seymour and Pease LLP; Mih Suhn Koh

(57) ABSTRACT

Provided is a mutant UDG having improved thermal sensitivity compared to a wild-type UDG. The mutant UDG of the presently claimed subject matter having a high thermal sensitivity has no inhibitory effect on the PCR reaction and thus can be advantageously used for the development of PCR/qPCR Premix and particularly PCR diagnostic kits employing UDG which requires the use of relatively low temperature in melting and amplification steps.

11 Claims, 25 Drawing Sheets

Specification includes a Sequence Listing.

(56) References Cited

PUBLICATIONS

Jaeger et al., "Molecular cloning, sequencing, and expression of the heat-labile uracil-DNA glycosylase from a marine psychrophilic bacterium, strain BMTU3346", Extremophiles, 2000, vol. 4, pp. 115-122.

Yamamoto, "PCR in Diagnosis of Infection: Detection of Bacteria in Cerebrospinal Fluids", Clinical and Diagnostic Laboratory Immunology, 2002, vol. 9, No. 3, pp. 508-514.

* cited by examiner

SEQUENCE LISTING

<160> NUMBER OF SEQ ID NOS: 161

<210> SEQ ID NO 1
<211> LENGTH: 229
<212> TYPE: PRT
<213> ORGANISM: Escherichia coli
<220> FEATURE:
<221> NAME/KEY: MISC_FEATURE
<222> LOCATION: (1)..(229)
<223> OTHER INFORMATION: Wild-type UDG

<400> SEQUENCE: 1

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 2
<211> LENGTH: 229
<212> TYPE: PRT
<213> ORGANISM: Artificial Sequence
<220> FEATURE:
<223> OTHER INFORMATION: Mutant UDG E4A

<400> SEQUENCE: 2

```
Met Ala Asn Ala Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
```

```
            50                  55                  60
Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Asn Thr Val Leu Thr Val
            115                 120                 125

Arg Ala Gly Gln Ala His Ser His Ala Ser Leu Gly Trp Glu Thr Phe
            130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
            210                 215                 220

Pro Ala Glu Ser Glu
225

<210> SEQ ID NO 3
<211> LENGTH: 229
<212> TYPE: PRT
<213> ORGANISM: Artificial Sequence
<220> FEATURE:
<223> OTHER INFORMATION: Mutant UDG W7A

<400> SEQUENCE: 3

Met Ala Asn Glu Leu Thr Ala His Asp Val Leu Ala Glu Glu Lys Gln
 1               5                  10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Asp Val Phe Asn Ala Phe
            35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Asn Thr Val Leu Thr Val
            115                 120                 125

Arg Ala Gly Gln Ala His Ser His Ala Ser Leu Gly Trp Glu Thr Phe
            130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
```

```
                    180                 185                 190
Ala His Arg Gly Phe Phe Gly Cys Asn His Phe Val Leu Ala Asn Gln
                195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 4
<211> LENGTH: 229
<212> TYPE: PRT
<213> ORGANISM: Artificial Sequence
<220> FEATURE:
<223> OTHER INFORMATION: Mutant UDG E13A

<400> SEQUENCE: 4

Met Ala Asn Glu Leu Thr Trp His Asp Val Leu Ala Ala Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Asp Val Phe Asn Ala Phe
            35                  40                  45

Arg Phe Thr Glu Leu Gly Asp Val Lys Val Val Ile Leu Gly Gln Asp
        50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
        130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
                195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 5
<211> LENGTH: 229
<212> TYPE: PRT
<213> ORGANISM: Artificial Sequence
<220> FEATURE:
<223> OTHER INFORMATION: Mutant UDG Q16A

<400> SEQUENCE: 5

Met Ala Asn Glu Leu Thr Trp His Asp Val Leu Ala Glu Glu Lys Ala
1               5                   10                  15
```

```
Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 6
<211> LENGTH: 229
<212> TYPE: PRT
<213> ORGANISM: Artificial Sequence
<220> FEATURE:
<223> OTHER INFORMATION: Mutant UDG Y19A

<400> SEQUENCE: 6

Met Ala Asn Glu Leu Thr Trp His Asp Val Leu Ala Glu Glu Lys Gln
 1               5                  10                  15

Gln Pro Ala Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140
```

```
Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 7
<211> LENGTH: 229
<212> TYPE: PRT
<213> ORGANISM: Artificial Sequence
<220> FEATURE:
<223> OTHER INFORMATION: Mutant UDG D43A

<400> SEQUENCE: 7

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Ala Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 8
<211> LENGTH: 229
<212> TYPE: PRT
<213> ORGANISM: Artificial Sequence
<220> FEATURE:

<223> OTHER INFORMATION: Mutant UDG D43C

<400> SEQUENCE: 8

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Cys Val Phe Asn Ala Phe
            35                  40                  45

Arg Phe Thr Glu Leu Gly Asp Val Lys Val Val Ile Leu Gly Gln Asp
        50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
        130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225
```

<210> SEQ ID NO 9
<211> LENGTH: 229
<212> TYPE: PRT
<213> ORGANISM: Artificial Sequence
<220> FEATURE:
<223> OTHER INFORMATION: Mutant UDG D43G

<400> SEQUENCE: 9

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Gly Val Phe Asn Ala Phe
            35                  40                  45

Arg Phe Thr Glu Leu Gly Asp Val Lys Val Val Ile Leu Gly Gln Asp
        50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110
```

```
Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 10
<211> LENGTH: 229
<212> TYPE: PRT
<213> ORGANISM: Artificial Sequence
<220> FEATURE:
<223> OTHER INFORMATION: Mutant UDG D43H

<400> SEQUENCE: 10

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys His Val Phe Asn Ala Phe
            35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 11
<211> LENGTH: 229
<212> TYPE: PRT
<213> ORGANISM: Artificial Sequence
<220> FEATURE:
<223> OTHER INFORMATION: Mutant UDG D43I

<400> SEQUENCE: 11

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Ile Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 12
<211> LENGTH: 229
<212> TYPE: PRT
<213> ORGANISM: Artificial Sequence
<220> FEATURE:
<223> OTHER INFORMATION: Mutant UDG D43K

<400> SEQUENCE: 12

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Lys Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg

-continued

```
                65                  70                  75                  80
Pro Gly Ile Ala Ile Pro Pro Ser Leu Leu Asn Met Tyr Lys Glu Leu
                    85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 13
<211> LENGTH: 229
<212> TYPE: PRT
<213> ORGANISM: Artificial Sequence
<220> FEATURE:
<223> OTHER INFORMATION: Mutant UDG D43P

<400> SEQUENCE: 13

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Pro Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                    85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
```

```
                195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 14
<211> LENGTH: 229
<212> TYPE: PRT
<213> ORGANISM: Artificial Sequence
<220> FEATURE:
<223> OTHER INFORMATION: Mutant UDG D43R

<400> SEQUENCE: 14

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Arg Val Phe Asn Ala Phe
            35                  40                  45

Arg Phe Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 15
<211> LENGTH: 229
<212> TYPE: PRT
<213> ORGANISM: Artificial Sequence
<220> FEATURE:
<223> OTHER INFORMATION: Mutant UDG D43V

<400> SEQUENCE: 15

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30
```

```
Ser Gly Val Thr Ile Tyr Pro Pro Gln Lys Val Val Phe Asn Ala Phe
         35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
             100                 105                 110

Ser Trp Ala Arg Gln Gly Val Leu Leu Leu Asn Thr Val Leu Thr Val
         115                 120                 125

Arg Ala Gly Gln Ala His Ser His Ala Ser Leu Gly Trp Glu Thr Phe
 130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 16
<211> LENGTH: 229
<212> TYPE: PRT
<213> ORGANISM: Artificial Sequence
<220> FEATURE:
<223> OTHER INFORMATION: Mutant UDG D43W

<400> SEQUENCE: 16

Met Ala Asn Glu Leu Thr Trp His Asp Val Leu Ala Glu Glu Lys Gln
1                5                  10                  15

Gln Pro Tyr Phe Leu Asn Thr Leu Gln Thr Val Ala Ser Glu Arg Gln
             20                  25                  30

Ser Gly Val Thr Ile Tyr Pro Pro Gln Lys Trp Val Phe Asn Ala Phe
         35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
             100                 105                 110

Ser Trp Ala Arg Gln Gly Val Leu Leu Leu Asn Thr Val Leu Thr Val
         115                 120                 125

Arg Ala Gly Gln Ala His Ser His Ala Ser Leu Gly Trp Glu Thr Phe
 130                 135                 140

Thr Asp Lys Val Ile Ser Leu Ile Asn Gln His Arg Glu Gly Val Val
145                 150                 155                 160
```

Phe Leu Leu Trp Gly Ser His Ala Gln Lys Lys Gly Ala Ile Ile Asp
                    165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 17
<211> LENGTH: 229
<212> TYPE: PRT
<213> ORGANISM: Artificial Sequence
<220> FEATURE:
<223> OTHER INFORMATION: Mutant UDG F48A

<400> SEQUENCE: 17

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Ala
        35                  40                  45

Arg Phe Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 18
<211> LENGTH: 229
<212> TYPE: PRT
<213> ORGANISM: Artificial Sequence
<220> FEATURE:
<223> OTHER INFORMATION: Mutant UDG F50A

<400> SEQUENCE: 18

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Ala Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 19
<211> LENGTH: 229
<212> TYPE: PRT
<213> ORGANISM: Artificial Sequence
<220> FEATURE:
<223> OTHER INFORMATION: Mutant UDG E52A

<400> SEQUENCE: 19

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Ala Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125
```

```
Arg Ala Gly Gln Ala His Ser His Ala Ser Leu Gly Trp Glu Thr Phe
            130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
            210                 215                 220

Pro Ala Glu Ser Glu
225

<210> SEQ ID NO 20
<211> LENGTH: 229
<212> TYPE: PRT
<213> ORGANISM: Artificial Sequence
<220> FEATURE:
<223> OTHER INFORMATION: Mutant UDG K57A

<400> SEQUENCE: 20

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Ala Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
            210                 215                 220

Pro Ala Glu Ser Glu
225

<210> SEQ ID NO 21
```

```
<211> LENGTH: 229
<212> TYPE: PRT
<213> ORGANISM: Artificial Sequence
<220> FEATURE:
<223> OTHER INFORMATION: Mutant UDG I60A

<400> SEQUENCE: 21

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ala Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 22
<211> LENGTH: 229
<212> TYPE: PRT
<213> ORGANISM: Artificial Sequence
<220> FEATURE:
<223> OTHER INFORMATION: Mutant UDG H67A

<400> SEQUENCE: 22

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr Ala Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
```

```
                    85                  90                  95
Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
        130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 23
<211> LENGTH: 229
<212> TYPE: PRT
<213> ORGANISM: Artificial Sequence
<220> FEATURE:
<223> OTHER INFORMATION: Mutant UDG Q71A

<400> SEQUENCE: 23

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
50                  55                  60

Pro Tyr His Gly Pro Gly Ala Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
        130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
```

Pro Ala Glu Ser Glu
225

<210> SEQ ID NO 24
<211> LENGTH: 229
<212> TYPE: PRT
<213> ORGANISM: Artificial Sequence
<220> FEATURE:
<223> OTHER INFORMATION: Mutant UDG H73A

<400> SEQUENCE: 24

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala Ala Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 25
<211> LENGTH: 229
<212> TYPE: PRT
<213> ORGANISM: Artificial Sequence
<220> FEATURE:
<223> OTHER INFORMATION: Mutant UDG F77A

<400> SEQUENCE: 25

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Ala Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 26
<211> LENGTH: 229
<212> TYPE: PRT
<213> ORGANISM: Artificial Sequence
<220> FEATURE:
<223> OTHER INFORMATION: Mutant UDG R80A

<400> SEQUENCE: 26

Met Ala Asn Glu Leu Thr Trp His Asp Val Leu Ala Glu Glu Lys Gln
 1               5                  10                  15

Gln Pro Tyr Phe Leu Asn Thr Leu Gln Thr Val Ala Ser Glu Arg Gln
             20                  25                  30

Ser Gly Val Thr Ile Tyr Pro Pro Gln Lys Asp Val Phe Asn Ala Phe
         35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Ala
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

```
Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 27
<211> LENGTH: 229
<212> TYPE: PRT
<213> ORGANISM: Artificial Sequence
<220> FEATURE:
<223> OTHER INFORMATION: Mutant UDG P87A

<400> SEQUENCE: 27

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Ala Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 28
<211> LENGTH: 229
<212> TYPE: PRT
<213> ORGANISM: Artificial Sequence
<220> FEATURE:
<223> OTHER INFORMATION: Mutant UDG L96A

<400> SEQUENCE: 28

Met Ala Asn Glu Leu Thr Trp His Asp Val Leu Ala Glu Glu Lys Gln
1               5                   10                  15
```

```
Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Ala
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 29
<211> LENGTH: 229
<212> TYPE: PRT
<213> ORGANISM: Artificial Sequence
<220> FEATURE:
<223> OTHER INFORMATION: Mutant UDG E97A

<400> SEQUENCE: 29

Met Ala Asn Glu Leu Thr Trp His Asp Val Leu Ala Glu Glu Lys Gln
 1               5                  10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                85                  90                  95

Ala Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
130                 135                 140
```

```
Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 30
<211> LENGTH: 229
<212> TYPE: PRT
<213> ORGANISM: Artificial Sequence
<220> FEATURE:
<223> OTHER INFORMATION: Mutant UDG N107A

<400> SEQUENCE: 30

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Ala His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 31
<211> LENGTH: 229
<212> TYPE: PRT
<213> ORGANISM: Artificial Sequence
<220> FEATURE:
<223> OTHER INFORMATION: Mutant UDG E112A

<400> SEQUENCE: 31

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Ala
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

<210> SEQ ID NO 32
<211> LENGTH: 229
<212> TYPE: PRT
<213> ORGANISM: Artificial Sequence
<220> FEATURE:
<223> OTHER INFORMATION: Mutant UDG L121A

<400> SEQUENCE: 32

```
Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
```

```
            100                 105                 110
Ser Trp Ala Arg Gln Gly Val Leu Ala Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 33
<211> LENGTH: 229
<212> TYPE: PRT
<213> ORGANISM: Artificial Sequence
<220> FEATURE:
<223> OTHER INFORMATION: Mutant UDG H134A

<400> SEQUENCE: 33

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala Ala Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
```

-continued

```
225

<210> SEQ ID NO 34
<211> LENGTH: 229
<212> TYPE: PRT
<213> ORGANISM: Artificial Sequence
<220> FEATURE:
<223> OTHER INFORMATION: Mutant UDG E142A

<400> SEQUENCE: 34

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Ala Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 35
<211> LENGTH: 229
<212> TYPE: PRT
<213> ORGANISM: Artificial Sequence
<220> FEATURE:
<223> OTHER INFORMATION: Mutant UDG F144A

<400> SEQUENCE: 35

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60
```

```
Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Ala
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
210                 215                 220

Pro Ala Glu Ser Glu
225

<210> SEQ ID NO 36
<211> LENGTH: 229
<212> TYPE: PRT
<213> ORGANISM: Artificial Sequence
<220> FEATURE:
<223> OTHER INFORMATION: Mutant UDG R156A

<400> SEQUENCE: 36

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
 65                 70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Ala Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190
```

Ala His Arg Gly Phe Phe Gly Cys Asn His Phe Val Leu Ala Asn Gln
                195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 37
<211> LENGTH: 229
<212> TYPE: PRT
<213> ORGANISM: Artificial Sequence
<220> FEATURE:
<223> OTHER INFORMATION: Mutant UDG E157A

<400> SEQUENCE: 37

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Ala Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 38
<211> LENGTH: 229
<212> TYPE: PRT
<213> ORGANISM: Artificial Sequence
<220> FEATURE:
<223> OTHER INFORMATION: Mutant UDG F161A

<400> SEQUENCE: 38

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
         35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Ala Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 39
<211> LENGTH: 229
<212> TYPE: PRT
<213> ORGANISM: Artificial Sequence
<220> FEATURE:
<223> OTHER INFORMATION: Mutant UDG L162A

<400> SEQUENCE: 39

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
         35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

```
Phe Ala Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 40
<211> LENGTH: 229
<212> TYPE: PRT
<213> ORGANISM: Artificial Sequence
<220> FEATURE:
<223> OTHER INFORMATION: Mutant UDG W164A

<400> SEQUENCE: 40

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Ala Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 41
<211> LENGTH: 229
<212> TYPE: PRT
<213> ORGANISM: Artificial Sequence
<220> FEATURE:
<223> OTHER INFORMATION: Mutant UDG K171A
```

<400> SEQUENCE: 41

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65              70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Ala Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 42
<211> LENGTH: 229
<212> TYPE: PRT
<213> ORGANISM: Artificial Sequence
<220> FEATURE:
<223> OTHER INFORMATION: Mutant UDG Q178A

<400> SEQUENCE: 42

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65              70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val

```
                115                 120                 125
Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Ala Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 43
<211> LENGTH: 229
<212> TYPE: PRT
<213> ORGANISM: Artificial Sequence
<220> FEATURE:
<223> OTHER INFORMATION: Mutant UDG R179A

<400> SEQUENCE: 43

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Ala His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225
```

```
<210> SEQ ID NO 44
<211> LENGTH: 229
<212> TYPE: PRT
<213> ORGANISM: Artificial Sequence
<220> FEATURE:
<223> OTHER INFORMATION: Mutant UDG H180A

<400> SEQUENCE: 44

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg Ala His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Gly Glu Thr Pro Ile Asp Trp Met Pro Val Leu
    210                 215                 220

Pro Ala Glu Ser Glu
225

<210> SEQ ID NO 45
<211> LENGTH: 229
<212> TYPE: PRT
<213> ORGANISM: Artificial Sequence
<220> FEATURE:
<223> OTHER INFORMATION: Mutant UDG L183A

<400> SEQUENCE: 45

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80
```

```
Pro Gly Ile Ala Ile Pro Pro Ser Leu Leu Asn Met Tyr Lys Glu Leu
            85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
            130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Ala Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Gly Glu Thr Pro Ile Asp Trp Met Pro Val Leu
            210                 215                 220

Pro Ala Glu Ser Glu
225

<210> SEQ ID NO 46
<211> LENGTH: 229
<212> TYPE: PRT
<213> ORGANISM: Artificial Sequence
<220> FEATURE:
<223> OTHER INFORMATION: Mutant UDG H202A

<400> SEQUENCE: 46

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
            35                  40                  45

Arg Phe Thr Glu Leu Gly Asp Val Lys Val Val Ile Leu Gly Gln Asp
50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
            85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
            115                 120                 125

Arg Ala Gly Gln Ala His Ser His Ala Ser Leu Gly Trp Glu Thr Phe
            130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn Ala Phe Val Leu Ala Asn Gln
            195                 200                 205
```

Trp Leu Glu Gln Arg Gly Glu Thr Pro Ile Asp Trp Met Pro Val Leu
    210                 215                 220

Pro Ala Glu Ser Glu
225

<210> SEQ ID NO 47
<211> LENGTH: 229
<212> TYPE: PRT
<213> ORGANISM: Artificial Sequence
<220> FEATURE:
<223> OTHER INFORMATION: Mutant UDG G214E

<400> SEQUENCE: 47

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Glu Glu Thr Pro Ile Asp Trp Met Pro Val Leu
    210                 215                 220

Pro Ala Glu Ser Glu
225

<210> SEQ ID NO 48
<211> LENGTH: 229
<212> TYPE: PRT
<213> ORGANISM: Artificial Sequence
<220> FEATURE:
<223> OTHER INFORMATION: Mutant UDG G214R

<400> SEQUENCE: 48

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

-continued

```
Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
        195                 200                 205

Trp Leu Glu Gln Arg Arg Glu Thr Pro Ile Asp Trp Met Pro Val Leu
210                 215                 220

Pro Ala Glu Ser Glu
225
```

<210> SEQ ID NO 49
<211> LENGTH: 229
<212> TYPE: PRT
<213> ORGANISM: Artificial Sequence
<220> FEATURE:
<223> OTHER INFORMATION: Mutant UDG G214W

<400> SEQUENCE: 49

```
Met Ala Asn Glu Leu Thr Trp His Asp Val Leu Ala Glu Glu Lys Gln
 1               5                  10                  15

Gln Pro Tyr Phe Leu Asn Thr Leu Gln Thr Val Ala Ser Glu Arg Gln
                 20                  25                  30

Ser Gly Val Thr Ile Tyr Pro Pro Gln Lys Asp Val Phe Asn Ala Phe
            35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                 85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175
```

```
Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Trp Glu Thr Pro Ile Asp Trp Met Pro Val Leu
    210                 215                 220

Pro Ala Glu Ser Glu
225

<210> SEQ ID NO 50
<211> LENGTH: 229
<212> TYPE: PRT
<213> ORGANISM: Artificial Sequence
<220> FEATURE:
<223> OTHER INFORMATION: Mutant UDG E215A

<400> SEQUENCE: 50

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
            20                  25                  30

Ser Gly Val Thr Ile Tyr Pro Pro Gln Lys Asp Val Phe Asn Ala Phe
        35                  40                  45

Arg Phe Thr Glu Leu Gly Asp Val Lys Val Val Ile Leu Gly Gln Asp
    50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
            100                 105                 110

Ser Trp Ala Arg Gln Gly Val Leu Leu Leu Asn Thr Val Leu Thr Val
        115                 120                 125

Arg Ala Gly Gln Ala His Ser His Ala Ser Leu Gly Trp Glu Thr Phe
    130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
            180                 185                 190

Ala His Arg Gly Phe Phe Gly Cys Asn His Phe Val Leu Ala Asn Gln
            195                 200                 205

Trp Leu Glu Gln Arg Gly Ala Thr Pro Ile Asp Trp Met Pro Val Leu
    210                 215                 220

Pro Ala Glu Ser Glu
225

<210> SEQ ID NO 51
<211> LENGTH: 229
<212> TYPE: PRT
<213> ORGANISM: Artificial Sequence
<220> FEATURE:
<223> OTHER INFORMATION: Mutant UDG W220A

<400> SEQUENCE: 51

Met Ala Asn Glu Leu Thr Trp His Asp Val Leu Ala Glu Glu Lys Gln
```

```
  1               5                   10                  15
Gln Pro Tyr Phe Leu Asn Thr Leu Gln Thr Val Ala Ser Glu Arg Gln
                20                  25                  30

Ser Gly Val Thr Ile Tyr Pro Pro Gln Lys Asp Val Phe Asn Ala Phe
                35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
                115                 120                 125

Arg Ala Gly Gln Ala His Ser His Ala Ser Leu Gly Trp Glu Thr Phe
 130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
                195                 200                 205

Trp Leu Glu Gln Arg Gly Glu Thr Pro Ile Asp Ala Met Pro Val Leu
 210                 215                 220

Pro Ala Glu Ser Glu
225
```

<210> SEQ ID NO 52
<211> LENGTH: 229
<212> TYPE: PRT
<213> ORGANISM: Artificial Sequence
<220> FEATURE:
<223> OTHER INFORMATION: Mutant UDG L224A

<400> SEQUENCE: 52

```
Met Ala Asn Glu Leu Thr Trp His Asp Val Leu Ala Glu Glu Lys Gln
 1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Asp Val Phe Asn Ala Phe
                35                  40                  45

Arg Phe Thr Glu Leu Gly Asp Val Lys Val Val Ile Leu Gly Gln Asp
 50                  55                  60

Pro Tyr His Gly Pro Gly Gln Ala His Gly Leu Ala Phe Ser Val Arg
 65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
                115                 120                 125

Arg Ala Gly Gln Ala His Ser His Ala Ser Leu Gly Trp Glu Thr Phe
```

```
                130                 135                 140
Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
                195                 200                 205

Trp Leu Glu Gln Arg Gly Glu Thr Pro Ile Asp Trp Met Pro Val Ala
                210                 215                 220

Pro Ala Glu Ser Glu
225

<210> SEQ ID NO 53
<211> LENGTH: 229
<212> TYPE: PRT
<213> ORGANISM: Artificial Sequence
<220> FEATURE:
<223> OTHER INFORMATION: Mutant UDG D43X
<220> FEATURE:
<221> NAME/KEY: MISC_FEATURE
<222> LOCATION: (43)
<223> OTHER INFORMATION: Xaa may be A, C, G, K, H, I P, R, V or W

<400> SEQUENCE: 53

Met Ala Asn Glu Leu Thr Trp His Asp Val Leu Ala Glu Glu Lys Gln
1               5                   10                  15

Gln Pro Tyr Phe Leu Asn Thr Leu Gln Thr Val Ala Ser Glu Arg Gln
                20                  25                  30

Ser Gly Val Thr Ile Tyr Pro Pro Gln Lys Xaa Val Phe Asn Ala Phe
                35                  40                  45

Arg Phe Thr Glu Leu Gly Asp Val Lys Val Val Ile Leu Gly Gln Asp
            50                  55                  60

Pro Tyr His Gly Pro Gly Gln Ala His Gly Leu Ala Phe Ser Val Arg
65                  70                  75                  80

Pro Gly Ile Ala Ile Pro Pro Ser Leu Leu Asn Met Tyr Lys Glu Leu
                85                  90                  95

Glu Asn Thr Ile Pro Gly Phe Thr Arg Pro Asn His Gly Tyr Leu Glu
                100                 105                 110

Ser Trp Ala Arg Gln Gly Val Leu Leu Leu Asn Thr Val Leu Thr Val
                115                 120                 125

Arg Ala Gly Gln Ala His Ser His Ala Ser Leu Gly Trp Glu Thr Phe
                130                 135                 140

Thr Asp Lys Val Ile Ser Leu Ile Asn Gln His Arg Glu Gly Val Val
145                 150                 155                 160

Phe Leu Leu Trp Gly Ser His Ala Gln Lys Lys Gly Ala Ile Ile Asp
                165                 170                 175

Lys Gln Arg His His Val Leu Lys Ala Pro His Pro Ser Pro Leu Ser
                180                 185                 190

Ala His Arg Gly Phe Phe Gly Cys Asn His Phe Val Leu Ala Asn Gln
                195                 200                 205

Trp Leu Glu Gln Arg Gly Glu Thr Pro Ile Asp Trp Met Pro Val Leu
                210                 215                 220

Pro Ala Glu Ser Glu
225
```

<210> SEQ ID NO 54
<211> LENGTH: 690
<212> TYPE: DNA
<213> ORGANISM: Escherichia coli
<220> FEATURE:
<221> NAME/KEY: source
<222> LOCATION: (1)..(690)
<223> OTHER INFORMATION: Wild-type UDG

<400> SEQUENCE: 54

```
atggctaacg aattaacctg gcatgacgtg ctggctgaag agaagcagca        50
accctatttt cttaataccc ttcagaccgt cgccagcgag cggcagtccg        100
gcgtcactat ctacccacca caaaaagatg tctttaacgc gttccgcttt        150
acagagttgg gtgacgttaa agtggtgatt ctcggccagg atccttatca        200
cggaccggga caggcgcatg gtctggcatt ttccgttcgt cccggcattg        250
ccattcctcc gtcattattg aatatgtata aagagctgga aaatactatt        300
ccgggcttca cccgccctaa tcatggttat cttgaaagct gggcgcgtca        350
gggcgttctg ctactcaata ctgtgttgac ggtacgcgca ggtcaggcgc        400
attcccacgc cagcctcggc tgggaaacct tcaccgataa agtgatcagc        450
ctgattaacc agcatcgcga aggcgtggtg ttttgttgt ggggatcgca        500
tgcgcaaaag aaaggggcga ttatagataa gcaacgccat catgtactga        550
aagcaccgca tccgtcgccg ctttcggcgc atcgtggatt ctttggctgc        600
aaccattttg tgctggcaaa tcagtggctg gaacaacgtg gcgagacgcc        650
gattgactgg atgccagtat taccggcaga gagtgagtaa              690
```

<210> SEQ ID NO 55
<211> LENGTH: 31
<212> TYPE: DNA
<213> ORGANISM: Artificial Sequence
<220> FEATURE:
<223> OTHER INFORMATION: Mutant UDG E4A Forward

<400> SEQUENCE: 55

```
gcattaacct ggcatgacgt gctggctgaa g                         31
```

<210> SEQ ID NO 56
<211> LENGTH: 34
<212> TYPE: DNA
<213> ORGANISM: Artificial Sequence
<220> FEATURE:
<223> OTHER INFORMATION: Mutant UDG E4A Reverse

<400> SEQUENCE: 56

```
gttagccatg ccaccaatct gttctctgtg agcc                      34
```

<210> SEQ ID NO 57
<211> LENGTH: 27
<212> TYPE: DNA
<213> ORGANISM: Artificial Sequence
<220> FEATURE:
<223> OTHER INFORMATION: Mutant UDG W7A Forward

<400> SEQUENCE: 57

```
gcgcatgacg tgctggctga agagaag                              27
```

<210> SEQ ID NO 58
<211> LENGTH: 35

```
<212> TYPE: DNA
<213> ORGANISM: Artificial Sequence
<220> FEATURE:
<223> OTHER INFORMATION: Mutant UDG W7A Reverse

<400> SEQUENCE: 58
ggttaattcg ttagccatcc caccaatctg ttctc                              35

<210> SEQ ID NO 59
<211> LENGTH: 35
<212> TYPE: DNA
<213> ORGANISM: Artificial Sequence
<220> FEATURE:
<223> OTHER INFORMATION: Mutant UDG E13A Forward

<400> SEQUENCE: 59
gcagagaagc agcaaccctg ttttcttaat accct                              35

<210> SEQ ID NO 60
<211> LENGTH: 26
<212> TYPE: DNA
<213> ORGANISM: Artificial Sequence
<220> FEATURE:
<223> OTHER INFORMATION: Mutant UDG E13A Reverse

<400> SEQUENCE: 60
agccagcacg tcatgccagg ttaatt                                        26

<210> SEQ ID NO 61
<211> LENGTH: 34
<212> TYPE: DNA
<213> ORGANISM: Artificial Sequence
<220> FEATURE:
<223> OTHER INFORMATION: Mutant UDG Q16A Forward

<400> SEQUENCE: 61
gcgcaaccct attttcttaa tacccttcag accg                               34

<210> SEQ ID NO 62
<211> LENGTH: 26
<212> TYPE: DNA
<213> ORGANISM: Artificial Sequence
<220> FEATURE:
<223> OTHER INFORMATION: Mutant UDG Q16A Reverse

<400> SEQUENCE: 62
cttctcttca gccagcacgt catgcc                                        26

<210> SEQ ID NO 63
<211> LENGTH: 32
<212> TYPE: DNA
<213> ORGANISM: Artificial Sequence
<220> FEATURE:
<223> OTHER INFORMATION: Mutant UDG Y19A Forward

<400> SEQUENCE: 63
gcttttctta ataccttca gaccgtcgcc ag                                  32

<210> SEQ ID NO 64
<211> LENGTH: 27
<212> TYPE: DNA
<213> ORGANISM: Artificial Sequence
<220> FEATURE:
<223> OTHER INFORMATION: Mutant UDG Y19A Reverse

<400> SEQUENCE: 64
```

-continued gggttgctgc ttctcttcag ccagcac                          27

<210> SEQ ID NO 65
<211> LENGTH: 30
<212> TYPE: DNA
<213> ORGANISM: Artificial Sequence
<220> FEATURE:
<223> OTHER INFORMATION: Mutant UDG D43A Forward

<400> SEQUENCE: 65
gctgtcttta acgcgttccg ctttacagag                       30

<210> SEQ ID NO 66
<211> LENGTH: 27
<212> TYPE: DNA
<213> ORGANISM: Artificial Sequence
<220> FEATURE:
<223> OTHER INFORMATION: Mutant UDG D43A Reverse

<400> SEQUENCE: 66
tttttgtggt gggtagatag tgacgcc                          27

<210> SEQ ID NO 67
<211> LENGTH: 30
<212> TYPE: DNA
<213> ORGANISM: Artificial Sequence
<220> FEATURE:
<223> OTHER INFORMATION: Mutant UDG D43C Forward

<400> SEQUENCE: 67
tgtgtcttta acgcgttccg ctttacagag                       30

<210> SEQ ID NO 68
<211> LENGTH: 28
<212> TYPE: DNA
<213> ORGANISM: Artificial Sequence
<220> FEATURE:
<223> OTHER INFORMATION: Mutant UDG D43C Reverse

<400> SEQUENCE: 68
tttttgtggt gggtagatag tgacgccg                         28

<210> SEQ ID NO 69
<211> LENGTH: 30
<212> TYPE: DNA
<213> ORGANISM: Artificial Sequence
<220> FEATURE:
<223> OTHER INFORMATION: Mutant UDG D43G Forward

<400> SEQUENCE: 69
ggtgtcttta acgcgttccg ctttacagag                       30

<210> SEQ ID NO 70
<211> LENGTH: 28
<212> TYPE: DNA
<213> ORGANISM: Artificial Sequence
<220> FEATURE:
<223> OTHER INFORMATION: Mutant UDG D43G Reverse

<400> SEQUENCE: 70
tttttgtggt gggtagatag tgacgccg                         28

<210> SEQ ID NO 71
<211> LENGTH: 30
<212> TYPE: DNA
<213> ORGANISM: Artificial Sequence

```
<220> FEATURE:
<223> OTHER INFORMATION: Mutant UDG D43H Forward

<400> SEQUENCE: 71
catgtcttta acgcgttccg ctttacagag                                   30

<210> SEQ ID NO 72
<211> LENGTH: 28
<212> TYPE: DNA
<213> ORGANISM: Artificial Sequence
<220> FEATURE:
<223> OTHER INFORMATION: Mutant UDG D43H Reverse

<400> SEQUENCE: 72
tttttgtggt gggtagatag tgacgccg                                     28

<210> SEQ ID NO 73
<211> LENGTH: 30
<212> TYPE: DNA
<213> ORGANISM: Artificial Sequence
<220> FEATURE:
<223> OTHER INFORMATION: Mutant UDG D43I Forward

<400> SEQUENCE: 73
attgtcttta acgcgttccg ctttacagag                                   30

<210> SEQ ID NO 74
<211> LENGTH: 28
<212> TYPE: DNA
<213> ORGANISM: Artificial Sequence
<220> FEATURE:
<223> OTHER INFORMATION: Mutant UDG D43I Reverse

<400> SEQUENCE: 74
tttttgtggt gggtagatag tgacgccg                                     28

<210> SEQ ID NO 75
<211> LENGTH: 30
<212> TYPE: DNA
<213> ORGANISM: Artificial Sequence
<220> FEATURE:
<223> OTHER INFORMATION: Mutant UDG D43K Forward

<400> SEQUENCE: 75
aaggtcttta acgcgttccg ctttacagag                                   30

<210> SEQ ID NO 76
<211> LENGTH: 28
<212> TYPE: DNA
<213> ORGANISM: Artificial Sequence
<220> FEATURE:
<223> OTHER INFORMATION: Mutant UDG D43K Reverse

<400> SEQUENCE: 76
tttttgtggt gggtagatag tgacgccg                                     28

<210> SEQ ID NO 77
<211> LENGTH: 30
<212> TYPE: DNA
<213> ORGANISM: Artificial Sequence
<220> FEATURE:
<223> OTHER INFORMATION: Mutant UDG D43P Forward

<400> SEQUENCE: 77
cctgtcttta acgcgttccg ctttacagag                                   30
```

-continued

```
<210> SEQ ID NO 78
<211> LENGTH: 28
<212> TYPE: DNA
<213> ORGANISM: Artificial Sequence
<220> FEATURE:
<223> OTHER INFORMATION: Mutant UDG D43P Reverse

<400> SEQUENCE: 78
tttttgtggt gggtagatag tgacgccg                                        28

<210> SEQ ID NO 79
<211> LENGTH: 37
<212> TYPE: DNA
<213> ORGANISM: Artificial Sequence
<220> FEATURE:
<223> OTHER INFORMATION: Mutant UDG D43R Forward

<400> SEQUENCE: 79
cgtgtcttta acgcgttccg ctttacagag ttgggtg                              37

<210> SEQ ID NO 80
<211> LENGTH: 35
<212> TYPE: DNA
<213> ORGANISM: Artificial Sequence
<220> FEATURE:
<223> OTHER INFORMATION: Mutant UDG D43R Reverse

<400> SEQUENCE: 80
tttttgtggt gggtagatag tgacgccgga ctgcc                                35

<210> SEQ ID NO 81
<211> LENGTH: 30
<212> TYPE: DNA
<213> ORGANISM: Artificial Sequence
<220> FEATURE:
<223> OTHER INFORMATION: Mutant UDG D43V Forward

<400> SEQUENCE: 81
gttgtcttta acgcgttccg ctttacagag                                      30

<210> SEQ ID NO 82
<211> LENGTH: 28
<212> TYPE: DNA
<213> ORGANISM: Artificial Sequence
<220> FEATURE:
<223> OTHER INFORMATION: Mutant UDG D43V Reverse

<400> SEQUENCE: 82
tttttgtggt gggtagatag tgacgccg                                        28

<210> SEQ ID NO 83
<211> LENGTH: 30
<212> TYPE: DNA
<213> ORGANISM: Artificial Sequence
<220> FEATURE:
<223> OTHER INFORMATION: Mutant UDG D43W Forward

<400> SEQUENCE: 83
tgggtcttta acgcgttccg ctttacagag                                      30

<210> SEQ ID NO 84
<211> LENGTH: 28
<212> TYPE: DNA
<213> ORGANISM: Artificial Sequence
<220> FEATURE:
<223> OTHER INFORMATION: Mutant UDG D43W Reverse
```

-continued

<400> SEQUENCE: 84 ttttttgtggt gggtagatag tgacgccg                                    28

<210> SEQ ID NO 85
<211> LENGTH: 33
<212> TYPE: DNA
<213> ORGANISM: Artificial Sequence
<220> FEATURE:
<223> OTHER INFORMATION: Mutant UDG F48A Forward

<400> SEQUENCE: 85
gcccgcttta cagagttggg tgacgttaaa gtg                               33

<210> SEQ ID NO 86
<211> LENGTH: 37
<212> TYPE: DNA
<213> ORGANISM: Artificial Sequence
<220> FEATURE:
<223> OTHER INFORMATION: Mutant UDG F48A Reverse

<400> SEQUENCE: 86
cgcgttaaag acatcttttt gtggtgggta gatagtg                           37

<210> SEQ ID NO 87
<211> LENGTH: 30
<212> TYPE: DNA
<213> ORGANISM: Artificial Sequence
<220> FEATURE:
<223> OTHER INFORMATION: Mutant UDG F50A Forward

<400> SEQUENCE: 87
gctacagagt gggtgacgt taaagtggtg                                    30

<210> SEQ ID NO 88
<211> LENGTH: 25
<212> TYPE: DNA
<213> ORGANISM: Artificial Sequence
<220> FEATURE:
<223> OTHER INFORMATION: Mutant UDG F50A Reverse

<400> SEQUENCE: 88
gcggaacgcg ttaaagacat ctttt                                        25

<210> SEQ ID NO 89
<211> LENGTH: 31
<212> TYPE: DNA
<213> ORGANISM: Artificial Sequence
<220> FEATURE:
<223> OTHER INFORMATION: Mutant UDG E52A Forward

<400> SEQUENCE: 89
gcgttgggtg acgttaaagt ggtgattctc g                                 31

<210> SEQ ID NO 90
<211> LENGTH: 35
<212> TYPE: DNA
<213> ORGANISM: Artificial Sequence
<220> FEATURE:
<223> OTHER INFORMATION: Mutant UDG E52A Reverse

<400> SEQUENCE: 90
tgtaaagcgg aacgcgttaa agacatcttt ttgtg                             35

<210> SEQ ID NO 91

```
<211> LENGTH: 28
<212> TYPE: DNA
<213> ORGANISM: Artificial Sequence
<220> FEATURE:
<223> OTHER INFORMATION: Mutant UDG K57A Forward

<400> SEQUENCE: 91
gcagtggtga ttctcggcca ggatcctt                                    28

<210> SEQ ID NO 92
<211> LENGTH: 25
<212> TYPE: DNA
<213> ORGANISM: Artificial Sequence
<220> FEATURE:
<223> OTHER INFORMATION: Mutant UDG K57A Reverse

<400> SEQUENCE: 92
aacgtcaccc aactctgtaa agcgg                                       25

<210> SEQ ID NO 93
<211> LENGTH: 26
<212> TYPE: DNA
<213> ORGANISM: Artificial Sequence
<220> FEATURE:
<223> OTHER INFORMATION: Mutant UDG I60A Forward

<400> SEQUENCE: 93
gctctcggcc aggatcctta tcacgg                                      26

<210> SEQ ID NO 94
<211> LENGTH: 32
<212> TYPE: DNA
<213> ORGANISM: Artificial Sequence
<220> FEATURE:
<223> OTHER INFORMATION: Mutant UDG I60A Reverse

<400> SEQUENCE: 94
caccacttta acgtcaccca actctgtaaa gc                               32

<210> SEQ ID NO 95
<211> LENGTH: 27
<212> TYPE: DNA
<213> ORGANISM: Artificial Sequence
<220> FEATURE:
<223> OTHER INFORMATION: Mutant UDG H67A Forward

<400> SEQUENCE: 95
gccggaccgg gacaggcgca tggtctg                                     27

<210> SEQ ID NO 96
<211> LENGTH: 39
<212> TYPE: DNA
<213> ORGANISM: Artificial Sequence
<220> FEATURE:
<223> OTHER INFORMATION: Mutant UDG H67A Reverse

<400> SEQUENCE: 96
ataaggatcc tggccgagaa tcaccacttt aacgtcacc                        39

<210> SEQ ID NO 97
<211> LENGTH: 29
<212> TYPE: DNA
<213> ORGANISM: Artificial Sequence
<220> FEATURE:
<223> OTHER INFORMATION: Mutant UDG Q71A Forward

<400> SEQUENCE: 97
```

-continued gcggcgcatg gtctggcatt ttccgttcg                      29

<210> SEQ ID NO 98
<211> LENGTH: 34
<212> TYPE: DNA
<213> ORGANISM: Artificial Sequence
<220> FEATURE:
<223> OTHER INFORMATION: Mutant UDG Q71A Reverse

<400> SEQUENCE: 98
tcccggtccg tgataaggat cctggccgag aatc                34

<210> SEQ ID NO 99
<211> LENGTH: 28
<212> TYPE: DNA
<213> ORGANISM: Artificial Sequence
<220> FEATURE:
<223> OTHER INFORMATION: Mutant UDG H73A Forward

<400> SEQUENCE: 99
gctggtctgg cattttccgt tcgtcccg                       28

<210> SEQ ID NO 100
<211> LENGTH: 30
<212> TYPE: DNA
<213> ORGANISM: Artificial Sequence
<220> FEATURE:
<223> OTHER INFORMATION: Mutant UDG H73A Reverse

<400> SEQUENCE: 100
cgcctgtccc ggtccgtgat aaggatcctg                     30

<210> SEQ ID NO 101
<211> LENGTH: 29
<212> TYPE: DNA
<213> ORGANISM: Artificial Sequence
<220> FEATURE:
<223> OTHER INFORMATION: Mutant UDG F77A Forward

<400> SEQUENCE: 101
gcttccgttc gtcccggcat tgccattcc                      29

<210> SEQ ID NO 102
<211> LENGTH: 27
<212> TYPE: DNA
<213> ORGANISM: Artificial Sequence
<220> FEATURE:
<223> OTHER INFORMATION: Mutant UDG F77A Reverse

<400> SEQUENCE: 102
tgccagacca tgcgcctgtc ccggtcc                        27

<210> SEQ ID NO 103
<211> LENGTH: 26
<212> TYPE: DNA
<213> ORGANISM: Artificial Sequence
<220> FEATURE:
<223> OTHER INFORMATION: Mutant UDG R80A Forward

<400> SEQUENCE: 103
gctcccggca ttgccattcc tccgtc                         26

<210> SEQ ID NO 104
<211> LENGTH: 29
<212> TYPE: DNA

<210> SEQ ID NO 104
<211> LENGTH: 29
<212> TYPE: DNA
<213> ORGANISM: Artificial Sequence
<220> FEATURE:
<223> OTHER INFORMATION: Mutant UDG R80A Reverse

<400> SEQUENCE: 104
aacggaaaat gccagaccat gcgcctgtc                                    29

<210> SEQ ID NO 105
<211> LENGTH: 43
<212> TYPE: DNA
<213> ORGANISM: Artificial Sequence
<220> FEATURE:
<223> OTHER INFORMATION: Mutant UDG P87A Forward

<400> SEQUENCE: 105
gcgtcattat tgaatatgta taaagagctg gaaaatacta ttc                    43

<210> SEQ ID NO 106
<211> LENGTH: 24
<212> TYPE: DNA
<213> ORGANISM: Artificial Sequence
<220> FEATURE:
<223> OTHER INFORMATION: Mutant UDG P87A Reverse

<400> SEQUENCE: 106
aggaatggca atgccgggac gaac                                         24

<210> SEQ ID NO 107
<211> LENGTH: 29
<212> TYPE: DNA
<213> ORGANISM: Artificial Sequence
<220> FEATURE:
<223> OTHER INFORMATION: Mutant UDG L96A Forward

<400> SEQUENCE: 107
gcggaaaata ctattccggg cttcacccg                                    29

<210> SEQ ID NO 108
<211> LENGTH: 41
<212> TYPE: DNA
<213> ORGANISM: Artificial Sequence
<220> FEATURE:
<223> OTHER INFORMATION: Mutant UDG L96A Reverse

<400> SEQUENCE: 108
ctctttatac atattcaata atgacggagg aatggcaatg c                      41

<210> SEQ ID NO 109
<211> LENGTH: 27
<212> TYPE: DNA
<213> ORGANISM: Artificial Sequence
<220> FEATURE:
<223> OTHER INFORMATION: Mutant UDG E97A Forward

<400> SEQUENCE: 109
gcaaatacta ttccgggctt cacccgc                                      27

<210> SEQ ID NO 110
<211> LENGTH: 35
<212> TYPE: DNA
<213> ORGANISM: Artificial Sequence
<220> FEATURE:
<223> OTHER INFORMATION: Mutant UDG E97A Reverse

<400> SEQUENCE: 110
cagctcttta tacatattca ataatgacgg aggaa                             35

<210> SEQ ID NO 111
<211> LENGTH: 29
<212> TYPE: DNA
<213> ORGANISM: Artificial Sequence
<220> FEATURE:
<223> OTHER INFORMATION: Mutant UDG N107A Forward

<400> SEQUENCE: 111
gctcatggtt atcttgaaag ctgggcgcg                                    29

<210> SEQ ID NO 112
<211> LENGTH: 26
<212> TYPE: DNA
<213> ORGANISM: Artificial Sequence
<220> FEATURE:
<223> OTHER INFORMATION: Mutant UDG N107A Reverse

<400> SEQUENCE: 112
agggcgggtg aagcccggaa tagtat                                       26

<210> SEQ ID NO 113
<211> LENGTH: 25
<212> TYPE: DNA
<213> ORGANISM: Artificial Sequence
<220> FEATURE:
<223> OTHER INFORMATION: Mutant UDG E112A Forward

<400> SEQUENCE: 113
gcaagctggg cgcgtcaggg cgttc                                        25

<210> SEQ ID NO 114
<211> LENGTH: 33
<212> TYPE: DNA
<213> ORGANISM: Artificial Sequence
<220> FEATURE:
<223> OTHER INFORMATION: Mutant UDG E112A Reverse

<400> SEQUENCE: 114
aagataacca tgattagggc gggtgaagcc cgg                               33

<210> SEQ ID NO 115
<211> LENGTH: 34
<212> TYPE: DNA
<213> ORGANISM: Artificial Sequence
<220> FEATURE:
<223> OTHER INFORMATION: Mutant UDG L121A Forward

<400> SEQUENCE: 115
gcactcaata ctgtgttgac ggtacgcgca ggtc                              34

<210> SEQ ID NO 116
<211> LENGTH: 27
<212> TYPE: DNA
<213> ORGANISM: Artificial Sequence
<220> FEATURE:
<223> OTHER INFORMATION: Mutant UDG L121A Reverse

<400> SEQUENCE: 116
cagaacgccc tgacgcgccc agctttc                                      27

<210> SEQ ID NO 117
<211> LENGTH: 25
<212> TYPE: DNA
<213> ORGANISM: Artificial Sequence
<220> FEATURE:

-continued

<223> OTHER INFORMATION: Mutant UDG H134A Forward

<400> SEQUENCE: 117
gcttcccacg ccagcctcgg ctggg                                25

<210> SEQ ID NO 118
<211> LENGTH: 29
<212> TYPE: DNA
<213> ORGANISM: Artificial Sequence
<220> FEATURE:
<223> OTHER INFORMATION: Mutant UDG H134A Reverse

<400> SEQUENCE: 118
cgcctgacct gcgcgtaccg tcaacacag                            29

<210> SEQ ID NO 119
<211> LENGTH: 36
<212> TYPE: DNA
<213> ORGANISM: Artificial Sequence
<220> FEATURE:
<223> OTHER INFORMATION: Mutant UDG E142A Forward

<400> SEQUENCE: 119
gcaaccttca ccgataaagt gatcagcctg attaac                    36

<210> SEQ ID NO 120
<211> LENGTH: 20
<212> TYPE: DNA
<213> ORGANISM: Artificial Sequence
<220> FEATURE:
<223> OTHER INFORMATION: Mutant UDG E142A Reverse

<400> SEQUENCE: 120
ccagccgagg ctggcgtggg                                      20

<210> SEQ ID NO 121
<211> LENGTH: 37
<212> TYPE: DNA
<213> ORGANISM: Artificial Sequence
<220> FEATURE:
<223> OTHER INFORMATION: Mutant UDG F144A Forward

<400> SEQUENCE: 121
gccaccgata aagtgatcag cctgattaac cagcatc                   37

<210> SEQ ID NO 122
<211> LENGTH: 25
<212> TYPE: DNA
<213> ORGANISM: Artificial Sequence
<220> FEATURE:
<223> OTHER INFORMATION: Mutant UDG F144A Reverse

<400> SEQUENCE: 122
ggtttcccag ccgaggctgg cgtgg                                25

<210> SEQ ID NO 123
<211> LENGTH: 27
<212> TYPE: DNA
<213> ORGANISM: Artificial Sequence
<220> FEATURE:
<223> OTHER INFORMATION: Mutant UDG R156A Forward

<400> SEQUENCE: 123
gccgaaggcg tggtgttttt gttgtgg                              27

```
<210> SEQ ID NO 124
<211> LENGTH: 30
<212> TYPE: DNA
<213> ORGANISM: Artificial Sequence
<220> FEATURE:
<223> OTHER INFORMATION: Mutant UDG R156A Reverse

<400> SEQUENCE: 124
atgctggtta atcaggctga tcactttatc                                    30

<210> SEQ ID NO 125
<211> LENGTH: 28
<212> TYPE: DNA
<213> ORGANISM: Artificial Sequence
<220> FEATURE:
<223> OTHER INFORMATION: Mutant UDG E157A Forward

<400> SEQUENCE: 125
gcaggcgtgg tgttttgtt gtggggat                                       28

<210> SEQ ID NO 126
<211> LENGTH: 30
<212> TYPE: DNA
<213> ORGANISM: Artificial Sequence
<220> FEATURE:
<223> OTHER INFORMATION: Mutant UDG E157A Reverse

<400> SEQUENCE: 126
gcgatgctgg ttaatcaggc tgatcacttt                                    30

<210> SEQ ID NO 127
<211> LENGTH: 30
<212> TYPE: DNA
<213> ORGANISM: Artificial Sequence
<220> FEATURE:
<223> OTHER INFORMATION: Mutant UDG F161A Forward

<400> SEQUENCE: 127
gctttgttgt ggggatcgca tgcgcaaaag                                    30

<210> SEQ ID NO 128
<211> LENGTH: 30
<212> TYPE: DNA
<213> ORGANISM: Artificial Sequence
<220> FEATURE:
<223> OTHER INFORMATION: Mutant UDG F161A Reverse

<400> SEQUENCE: 128
caccacgcct cgcgatgct ggttaatcag                                     30

<210> SEQ ID NO 129
<211> LENGTH: 25
<212> TYPE: DNA
<213> ORGANISM: Artificial Sequence
<220> FEATURE:
<223> OTHER INFORMATION: Mutant UDG L162A Forward

<400> SEQUENCE: 129
gcgttgtggg gatcgcatgc gcaaa                                         25

<210> SEQ ID NO 130
<211> LENGTH: 26
<212> TYPE: DNA
<213> ORGANISM: Artificial Sequence
<220> FEATURE:
<223> OTHER INFORMATION: Mutant UDG L162A Reverse
```

```
<400> SEQUENCE: 130
aaacaccacg ccttcgcgat gctggt                                            26

<210> SEQ ID NO 131
<211> LENGTH: 26
<212> TYPE: DNA
<213> ORGANISM: Artificial Sequence
<220> FEATURE:
<223> OTHER INFORMATION: Mutant UDG W164A Forward

<400> SEQUENCE: 131
gcgggatcgc atgcgcaaaa gaaagg                                            26

<210> SEQ ID NO 132
<211> LENGTH: 25
<212> TYPE: DNA
<213> ORGANISM: Artificial Sequence
<220> FEATURE:
<223> OTHER INFORMATION: Mutant UDG W164A Reverse

<400> SEQUENCE: 132
caacaaaaac accacgcctt cgcga                                             25

<210> SEQ ID NO 133
<211> LENGTH: 31
<212> TYPE: DNA
<213> ORGANISM: Artificial Sequence
<220> FEATURE:
<223> OTHER INFORMATION: Mutant UDG K171A Forward

<400> SEQUENCE: 133
gcaggggcga ttatagataa gcaacgccat c                                      31

<210> SEQ ID NO 134
<211> LENGTH: 25
<212> TYPE: DNA
<213> ORGANISM: Artificial Sequence
<220> FEATURE:
<223> OTHER INFORMATION: Mutant UDG K171A Reverse

<400> SEQUENCE: 134
cttttgcgca tgcgatcccc acaac                                             25

<210> SEQ ID NO 135
<211> LENGTH: 27
<212> TYPE: DNA
<213> ORGANISM: Artificial Sequence
<220> FEATURE:
<223> OTHER INFORMATION: Mutant UDG Q178A Forward

<400> SEQUENCE: 135
gcacgccatc atgtactgaa agcaccg                                           27

<210> SEQ ID NO 136
<211> LENGTH: 30
<212> TYPE: DNA
<213> ORGANISM: Artificial Sequence
<220> FEATURE:
<223> OTHER INFORMATION: Mutant UDG Q178A Reverse

<400> SEQUENCE: 136
cttatctata atcgcccctt tcttttgcgc                                        30

<210> SEQ ID NO 137
<211> LENGTH: 29
```

```
<212> TYPE: DNA
<213> ORGANISM: Artificial Sequence
<220> FEATURE:
<223> OTHER INFORMATION: Mutant UDG R179A Forward

<400> SEQUENCE: 137
gcccatcatg tactgaaagc accgcatcc                                    29

<210> SEQ ID NO 138
<211> LENGTH: 31
<212> TYPE: DNA
<213> ORGANISM: Artificial Sequence
<220> FEATURE:
<223> OTHER INFORMATION: Mutant UDG R179A Reverse

<400> SEQUENCE: 138
ttgcttatct ataatcgccc ctttcttttg c                                 31

<210> SEQ ID NO 139
<211> LENGTH: 27
<212> TYPE: DNA
<213> ORGANISM: Artificial Sequence
<220> FEATURE:
<223> OTHER INFORMATION: Mutant UDG H180A Forward

<400> SEQUENCE: 139
gctcatgtac tgaaagcacc gcatccg                                      27

<210> SEQ ID NO 140
<211> LENGTH: 28
<212> TYPE: DNA
<213> ORGANISM: Artificial Sequence
<220> FEATURE:
<223> OTHER INFORMATION: Mutant UDG H180A Reverse

<400> SEQUENCE: 140
gcgttgctta tctataatcg cccctttc                                     28

<210> SEQ ID NO 141
<211> LENGTH: 28
<212> TYPE: DNA
<213> ORGANISM: Artificial Sequence
<220> FEATURE:
<223> OTHER INFORMATION: Mutant UDG L183A Forward

<400> SEQUENCE: 141
gcgaaagcac cgcatccgtc gccgcttt                                     28

<210> SEQ ID NO 142
<211> LENGTH: 37
<212> TYPE: DNA
<213> ORGANISM: Artificial Sequence
<220> FEATURE:
<223> OTHER INFORMATION: Mutant UDG L183A Reverse

<400> SEQUENCE: 142
tacatgatgg cgttgcttat ctataatcgc ccctttc                           37

<210> SEQ ID NO 143
<211> LENGTH: 27
<212> TYPE: DNA
<213> ORGANISM: Artificial Sequence
<220> FEATURE:
<223> OTHER INFORMATION: Mutant UDG H202A Forward

<400> SEQUENCE: 143
```
gcttttgtgc tggcaaatca gtggctg                                         27

<210> SEQ ID NO 144
<211> LENGTH: 25
<212> TYPE: DNA
<213> ORGANISM: Artificial Sequence
<220> FEATURE:
<223> OTHER INFORMATION: Mutant UDG H202A Reverse

<400> SEQUENCE: 144
gttgcagcca aagaatccac gatgc                                           25

<210> SEQ ID NO 145
<211> LENGTH: 36
<212> TYPE: DNA
<213> ORGANISM: Artificial Sequence
<220> FEATURE:
<223> OTHER INFORMATION: Mutant UDG G214E Forward

<400> SEQUENCE: 145
gaggagacgc cgattgactg gatgccagta ttaccg                               36

<210> SEQ ID NO 146
<211> LENGTH: 36
<212> TYPE: DNA
<213> ORGANISM: Artificial Sequence
<220> FEATURE:
<223> OTHER INFORMATION: Mutant UDG G214E Reverse

<400> SEQUENCE: 146
acgttgttcc agccactgat ttgccagcac aaaatg                               36

<210> SEQ ID NO 147
<211> LENGTH: 28
<212> TYPE: DNA
<213> ORGANISM: Artificial Sequence
<220> FEATURE:
<223> OTHER INFORMATION: Mutant UDG G214R Forward

<400> SEQUENCE: 147
cgcgagacgc cgattgactg gatgccag                                        28

<210> SEQ ID NO 148
<211> LENGTH: 36
<212> TYPE: DNA
<213> ORGANISM: Artificial Sequence
<220> FEATURE:
<223> OTHER INFORMATION: Mutant UDG G214R Reverse

<400> SEQUENCE: 148
acgttgttcc agccactgat ttgccagcac aaaatg                               36

<210> SEQ ID NO 149
<211> LENGTH: 35
<212> TYPE: DNA
<213> ORGANISM: Artificial Sequence
<220> FEATURE:
<223> OTHER INFORMATION: Mutant UDG G214W Forward

<400> SEQUENCE: 149
tgggagacgc cgattgactg gatgccagta ttacc                                35

<210> SEQ ID NO 150
<211> LENGTH: 36
<212> TYPE: DNA
<213> ORGANISM: Artificial Sequence

```
<220> FEATURE:
<223> OTHER INFORMATION: Mutant UDG G214W Reverse

<400> SEQUENCE: 150
acgttgttcc agccactgat ttgccagcac aaaatg                                   36

<210> SEQ ID NO 151
<211> LENGTH: 28
<212> TYPE: DNA
<213> ORGANISM: Artificial Sequence
<220> FEATURE:
<223> OTHER INFORMATION: Mutant UDG E215A Forward

<400> SEQUENCE: 151
gcgacgccga ttgactggat gccagtat                                           28

<210> SEQ ID NO 152
<211> LENGTH: 26
<212> TYPE: DNA
<213> ORGANISM: Artificial Sequence
<220> FEATURE:
<223> OTHER INFORMATION: Mutant UDG E215A Reverse

<400> SEQUENCE: 152
gccacgttgt tccagccact gatttg                                             26

<210> SEQ ID NO 153
<211> LENGTH: 30
<212> TYPE: DNA
<213> ORGANISM: Artificial Sequence
<220> FEATURE:
<223> OTHER INFORMATION: Mutant UDG W220A Forward

<400> SEQUENCE: 153
gcgatgccag tattaccggc agagagtgag                                         30

<210> SEQ ID NO 154
<211> LENGTH: 22
<212> TYPE: DNA
<213> ORGANISM: Artificial Sequence
<220> FEATURE:
<223> OTHER INFORMATION: Mutant UDG W220A Reverse

<400> SEQUENCE: 154
gtcaatcggc gtctcgccac gt                                                 22

<210> SEQ ID NO 155
<211> LENGTH: 31
<212> TYPE: DNA
<213> ORGANISM: Artificial Sequence
<220> FEATURE:
<223> OTHER INFORMATION: Mutant UDG L224A Forward

<400> SEQUENCE: 155
gcaccggcag agagtgagta aatggctaac g                                       31

<210> SEQ ID NO 156
<211> LENGTH: 25
<212> TYPE: DNA
<213> ORGANISM: Artificial Sequence
<220> FEATURE:
<223> OTHER INFORMATION: Mutant UDG L224A Reverse

<400> SEQUENCE: 156
tactggcatc cagtcaatcg gcgtc                                              25
```

```
<210> SEQ ID NO 157
<211> LENGTH: 21
<212> TYPE: DNA
<213> ORGANISM: Artificial Sequence
<220> FEATURE:
<223> OTHER INFORMATION: Mutant UDG GAPDH Forward

<400> SEQUENCE: 157
acggatttgg tcgtattggg c                                            21

<210> SEQ ID NO 158
<211> LENGTH: 21
<212> TYPE: DNA
<213> ORGANISM: Artificial Sequence
<220> FEATURE:
<223> OTHER INFORMATION: Mutant UDG GAPDH Reverse

<400> SEQUENCE: 158
ttgacggtgc catggaattt g                                            21

<210> SEQ ID NO 159
<211> LENGTH: 24
<212> TYPE: DNA
<213> ORGANISM: Artificial Sequence
<220> FEATURE:
<223> OTHER INFORMATION: Mutant UDG GAPDH Probe

<400> SEQUENCE: 159
cctggtcacc agggctgctt ttaa                                         24

<210> SEQ ID NO 160
<211> LENGTH: 21
<212> TYPE: DNA
<213> ORGANISM: Artificial Sequence
<220> FEATURE:
<223> OTHER INFORMATION: Mutant UDG D43X Substrate 1

<400> SEQUENCE: 160
ggaacaattc ugcggcttta g                                            21

<210> SEQ ID NO 161
<211> LENGTH: 21
<212> TYPE: DNA
<213> ORGANISM: Artificial Sequence
<220> FEATURE:
<223> OTHER INFORMATION: Mutant UDG D43X Substrate 2

<400> SEQUENCE: 161
ctaaagccgc agaattgttc c                                            21
```

MUTANT URACIL DNA GLYCOSYLASE WITH IMPROVED THERMAL SENSITIVITY

SEQUENCE LISTING

The Sequence Listing submitted in text format (.txt) filed on Jan. 29, 2021, named "SequenceListing.txt", created on Jan. 29, 2021 (123,991 bytes), is incorporated herein by reference.

TECHNICAL FIELD

The present invention relates to UDG mutants with improved thermal sensitivity and its use.

BACKGROUND ART

PCR (Polymerase Chain Reaction) is a method to amplifying a particular nucleic acids of interest and one of the major methods for this purposes in the field of biology, biochemistry and medical field (Yamamoto, Y. Clin. Diagn. Lab. Immunol. 2002, 9 (3), 508-514).

PCR allows a very sensitive and rapid molecular diagnostic test, but there is a high possibility of a false-positive problem because the target to be detected are identical to the product amplified by PCR, both of which are DNA. In particular, false-positive amplification may occur due to the PCR product amplified in a previous reaction or carryover contamination generated during the processing of the sample. In the case of diagnostic laboratories that routinely perform PCR based diagnostic tests, PCR based tests using the same primers are repeated thousands to tens of thousands of times, so there have been various reports that the PCR products amplified in the previous reactions float in the air in the form of an aerosol, etc. and contaminate the samples to be tested causing false-positive amplification.

The carryover contamination by the PCR amplification products once occurs, the amount of the amplification product increases astronomically (about $10^{13}$ times compared to the initial DNA), so there is a problem that it is difficult to remove the contamination by conventional decontamination methods. Carryover contamination can cause serious problems by misdiagnosing an uninfected person as infected or inflicted with a particular disease. The amplified DNA products from a previous reaction could get mixed up with a sample for other tests, which may lead to a false result diagnosing a healthy person as a patient, resulting in incorrect prescription and treatment.

At present the most widely used methods to solve such carryover contamination is to use an Uracil DNA Glycosylase (UDG) in PCR reaction. In such methods, a mixture of dTTP/dUTP is used for a PCR reaction thus the amplification products containing both T and U are produced. From the subsequent PCR reactions, UDG is added to the PCR reaction mixture and the mixture is incubated at 37-50° C. for 5-30 minutes before the PCR reaction is performed for diagnosis. Through this process, the carryover contaminants, if present in the next PCR sample, contain dU, which are then removed by UDG. The contaminated DNAs from which dUs are removed by UDG are unstable and degraded into short fragments, which cannot be used as a template for PCR amplification.

Treatment of samples with UDG can be conveniently combined with the PCR by using a reaction mixture containing necessary reagents (UDG enzymes, dUTP) and adding one extra step before the general PCR is started. By this way, a carryover contamination can be conveniently prevented in a single reaction/single process.

However, the UDG enzymes currently widely used are from *Escherichia coli*, and are known to have a high thermal stability. This causes a problem of UDG being active even after the PCR reaction is complete. Thus, if the PCR reaction products are not purified by such as agarose gel electrophoresis right after the PCR completion, the reaction products are often degraded.

Further, in case of the complex multiplex real-time PCR, the reaction often needs be performed at a relatively low annealing temperature (about 50° C.) because of the use of TaqMan® probe, in which case, the use of UDG from *E. coli* causes a problem of decreasing the sensitivity of PCR (delay of Ct value) by degrading the amplicons because the activity of UDG from *E. coli* is remained after the completion of PCR. This is also a reason for negatively affecting the performance of PCR based diagnostic kits.

An example of a UDG derived from a microorganism that exhibits optimal activity at a relatively low temperature is marine UDG derived from the BMTU 3346 strain (Jaeger, S, Molecular cloning, sequency, and expression of the heat-labile uracil-DNA glycosylase from a marine psychrophilic bacterium, strain BMTU3346. Extremophiles. 2000, 4(2): 115-122). However, since this is expressed as a recombinant form in *E. coli*, not in the original strain, it has a low yield and solubility compared to *E. coli* UDG, resulting in high purification cost per unit enzyme and relatively complicated purification process.

Therefore, there is a need to develop a UDG that has a high thermal sensitivity and thus can be easily inactivated by heat during reaction processes such as PCR, and not reactivated once inactivated.

SUMMARY

Aspect of the present disclosure allows a UDG with high thermal sensitivity (also refer to as thermal liability) which is easily inactivated by heat during the PCR process and not reactivated once it is inactivated.

In one aspect of the present disclosure, there is provided an isolated mutant UDG with thermal sensitivity, derived from *Escherichia coli* comprising the amino acid sequence set forth in SEQ ID NO: 1 having at least one amino acid substitution, the substitution being selected from the group consisting of E4A, W7A, E13A, Q16A, Y19A, D43X, F48A, F50A, E52A, H67A, K57A, Q71A, H73A, P87A, L96A, E112A, L121A, H134A, E142A, F144A, R156A, F161A, L162A, W164A, H180A, L183A, H202A, G214E, G214W, G214R, W220A, and L224A, in which the number indicates the position of the substituted amino acid and the amino acids are indicated as a single letter code and X indicates any amino acids, in which the codes on the left and right sides of the position indicate a wild type and substituted residues, respectively.

In one embodiment, the present UDG polypeptide comprises a substitution at the position 43 and the amino acids substituting the position 43 is selected from the group consisting of A, C, G, H, I, K, P, R, V and W residues.

In view of the amino acids substituted at the position 43 in the present disclosure and very highly conserved substitutions, highly conserved substitutions and conserved substitutions of Table 2, it is clear to one of ordinary skill in the art that the position 43 may be substituted with, S, T, N, Q, E, Y, L, M, or F in addition to A, C, G, K, H, I, P, R, V and W to the UDG of the present effect.

In other embodiment, the present UDG polypeptide has a substitution that is selected from the group consisting of D43A, D43C, D43H, D43R, D43V, D43W and K57A.

In still other embodiment, the present UDG polypeptide further comprises E157A or E215A substitution.

In still other embodiment, the present UDG polypeptide comprises a combination of at least two substations and are selected from the group consisting of D43A/K57A, D43A/E157A, D43A/E215A, D43A/K57A/E157A, D43A/E157A/E215A, and D43A/K57A/E157A/E215A.

In other aspect, there is provided a kit comprising the present mutant UDG for removing nucleic acid contaminants in the sample/reaction mixture/template for RT, PCR or RT-PCR.

In still other aspect, there is provided a premixed composition for PCR comprising the present mutant UDG, a polymerase and a buffer for PCR.

In still other aspect, there is provided a premixed composition for RT (Reverse Transcription) comprising the present mutant UDG, a reverse transcriptase and a buffer for RT.

In still other aspect, there is provided a premixed composition for RT-PCR comprising the present mutant UDG, a reverse transcriptase, a polymerase and a buffer for RT-PCR.

In still other aspect, there is provided a method of removing/decontaminating a nucleic acid contaminant included in the sample/reaction mixture/reactant/template to be analyzed comprising a step of incubating the sample/reaction mixture/reactant/template with at least one of the present UDG at about at a temperature of 5 to 55° C.

In one embodiment, the sample/reaction mixture/reactant/template is analyzed by RT, PCR or RT-PCR.

In still other aspect, there is provided a nucleic acid encoding the present UDGs, a vector comprising the nucleic acid, and a cell transformed with the vector.

The present mutant UDGs show a high thermal sensitivity compared to a wild-type UDG and UDG commercially available, and thus can by effectively inactivated in the subsequent PCR reaction. As such, the present mutant UDGs, which do not interfere with PCR reactions, can be effectively used for the development of a premix for RT (Reverse Transcription), PCR (Polymerase Chain Reaction), RT-PCR or quantitative PCR (qPCR) and particularly for PCR diagnostic kits employing UDG which requires the use of a relatively low temperature in melting and amplification steps.

DETAILED DESCRIPTION OF EMBODIMENTS

Figure 1:
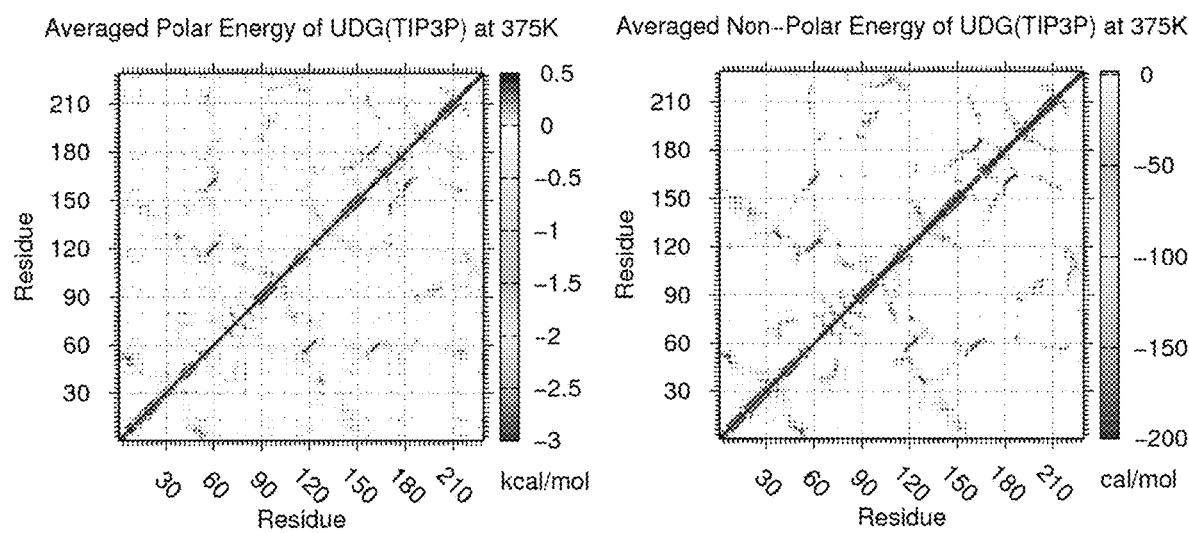
FIG. 1 is an energy network graph drawn from molecular dynamics to screen the residues for substitution to increase thermal sensitivity.
Figure 2A:
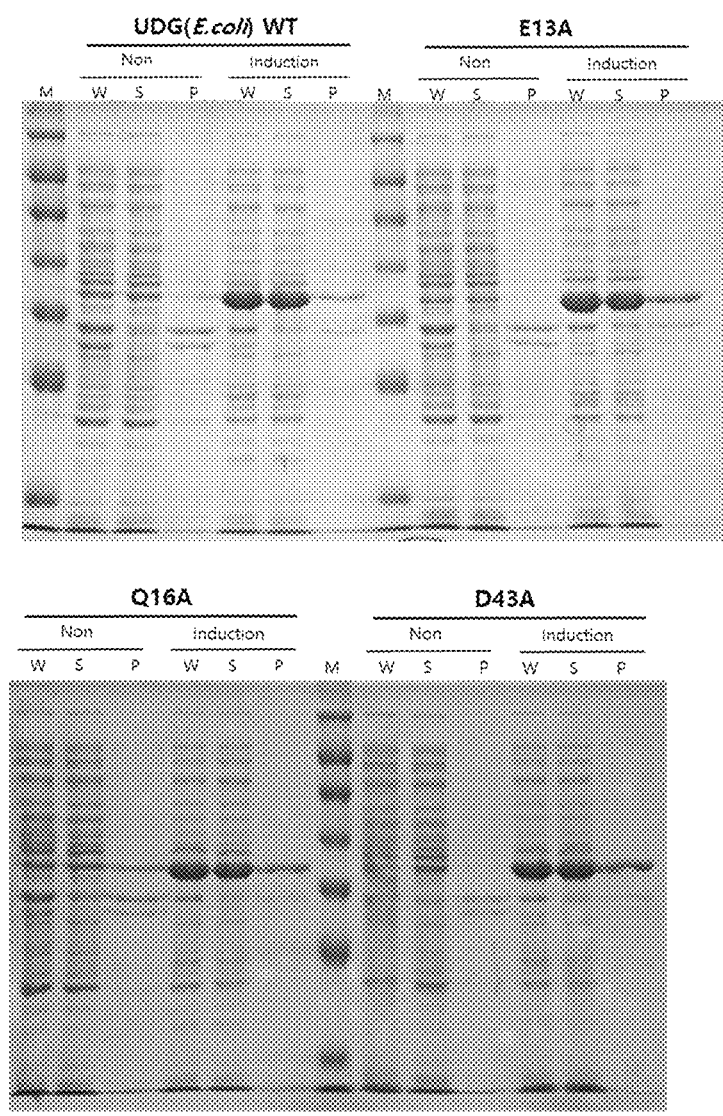
FIG. 2A to FIG. 2F are the result of SDS-PAGE showing the recombinant protein at issue is expressed in *E. coli* transformed with a vector having the gene encoding the mutant UDG protein prepared in accordance with one embodiment of the present invention.
Figure 2B:
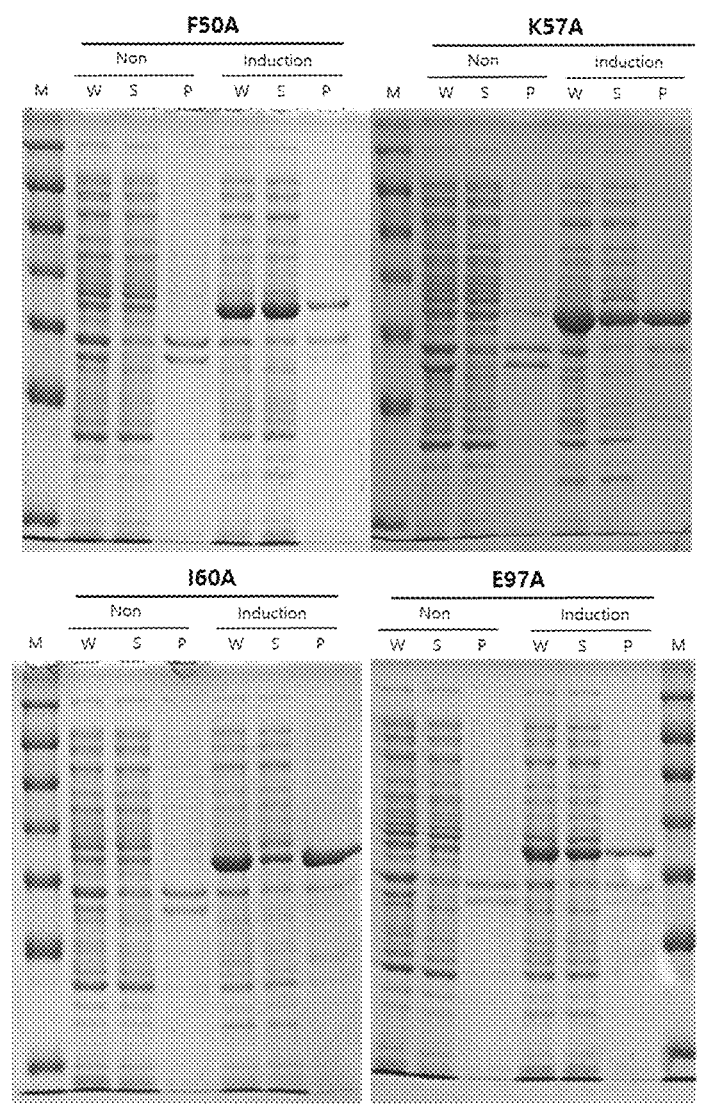
Figure 2C:
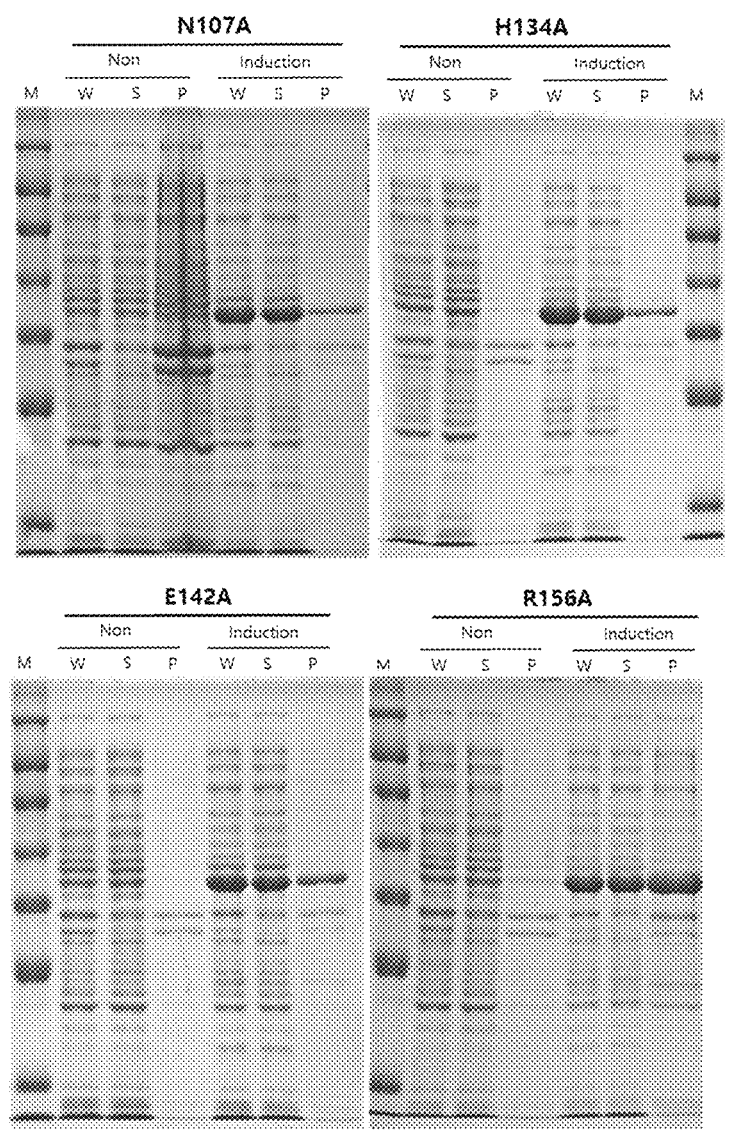
Figure 2D:
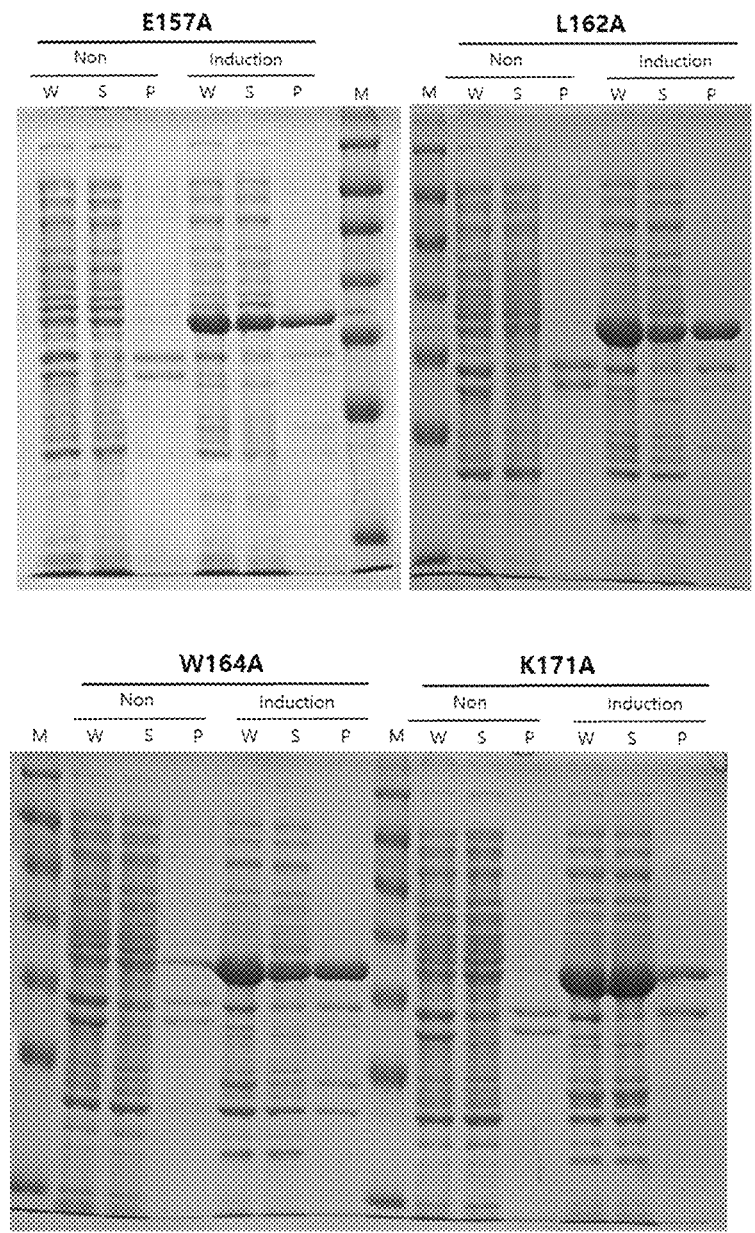
Figure 2E:
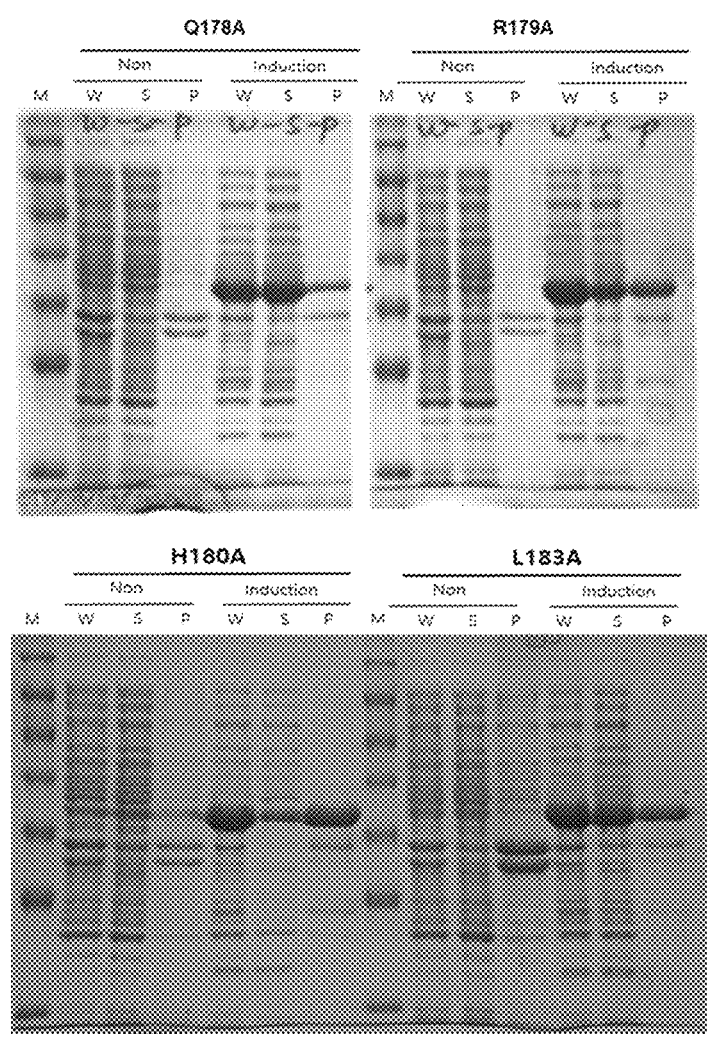
Figure 2F:
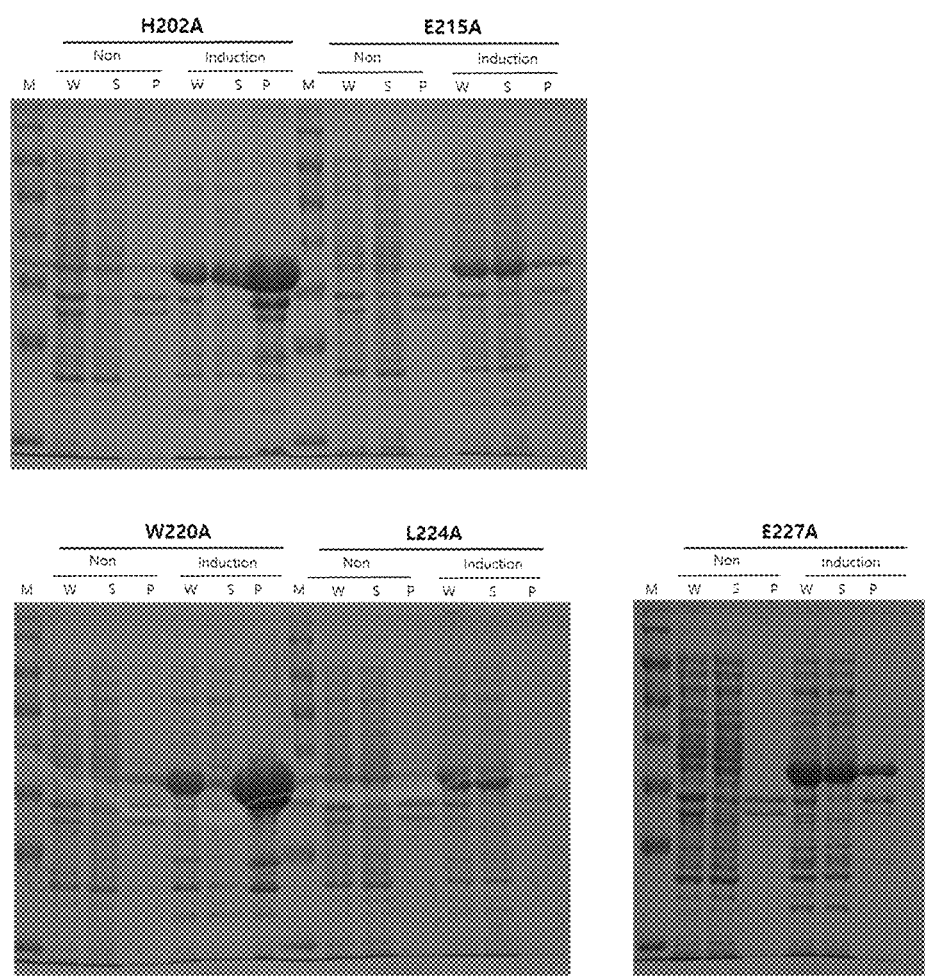

The present disclosure is based on the discovery and development of the mutant UDG proteins with improved thermal sensitivity by introducing various substitutions to the specific residues of *E. coli* UDG (Uracil DNA glycosylases).

In an amplification reaction such as PCR, the amplified products that have been produced in previous amplifications often contaminates a PCR specimen and the contaminants, not an actual template, are amplified in a subsequent PCR, resulting in false positives. To prevent this, usually the amplified DNA is made to contain dUTP during PCR, and then the amplified DNA if it contaminates a new amplification reaction is removed by treatment the sample with UDG at the beginning of a reaction. Then the UDG needs be inactivated for the optimal PCR efficiency. But if the thermal sensitivity of the UDG is low, the UDG activity is remained during the PCR and it causes a problem of reducing the amplification efficiency of PCR.

In the present disclosure, by introducing a substitution mutation into the specific residues of *E. coli* UDG, the thermal sensitivity of the present UDGs is improved compared to that of the wild type, and the present UDGs are completely inactivated in the subsequent PCR reaction performed at a relatively low temperature and thus solved the problem of reducing the PCR efficiency by wild-type UDG.

In one aspect of the present disclosure, there are provided isolated mutant UDG (Uracil DNA Glycosylase) polypeptides with improved thermal sensitivity compared to that of the wild-type UDG from *E. coli*, each of the mutant UDG having at least one amino acid substitution in the *E. coli* UDG, wherein the *E. coli* UDG is represented by the amino acid sequence set forth in SEQ ID NO: 1, and the at least one substitution is selected from the group consisting of E4A, W7A, E13A, Q16A, Y19A, D43X, F48A, F50A, E52A, H67A, K57A, Q71A, H73A, P87A, L96A, E112A, L121A, H134A, E142A, F144A, R156A, F161A, L162A, W164A, H180A, L183A, H202A, G214E, G214W, G214R, W220A, and L224A in which the number indicates the position of the substituted amino acid and the amino acids are indicated as a single letter code and X indicates any amino acids as describe below, in which the codes on the left and right sides of the position indicate a wild type and substituted residues, respectively, In the present disclosure, amino acids are denoted by a single letter code defined in the related art as follows: A, Alanine; R, Arginine; N, Asparagine; D, Aspartic acid; C, Cysteine; E, Glutamic acid; Q, Glutamine; G, Glycine; H, Histidine; I, Isoleucine; L, Leucine; K, Lysine; M, Methionine; F, Phenylalanine; P, Proline; S, Serine; T, Threonine; W, Tryptophan; Y, Tyrosine; V, Valine; Z, Glutamic acid and Glutamine; X, any amino acids.

As used herein the term "Uracil DNA glycosylases (UDG)" refers to an enzyme that cleaves a glycosidic bond between an Uracil and a deoxyribose when dUTPs are incorporated into DNA during the DNA synthesis and does not act on free dUTPs, free deoxyuridines and RNAs.

In one embodiment, the mutant UDG polypeptide according to the present disclosure includes the ones with at least one amino acid substitution at position 43 (the position indicated is based on the sequence set forth SEQ ID NO: 1). It was found in the present disclosure that through multiple sequence alignments of various enzymes with high structural similarity to *E. coli* UDGs and stability analysis using a commercial web server, the substitution at the position D43 and the amino acids substituting D43 are crucial for reducing the thermal stability. In the present disclosure, the wild-type aspartic acid residue (D) at the position 43 is substituted with A, C, G, K, H, I, P, R, V or W to obtain the mutant UDGs with improved thermal sensitivity. A person having ordinary skill in the related art would understand that the amino acids as described above are able to represent the 20 amino acids which may be grouped by their chemical or biochemical characteristics such as charges of the side chain constituting amino acids into several groups. Thus, the present mutant UDGs with substitution at the position 43 may also include the ones substituted with the amino acids other than the amino acids as described above.

In another embodiment, the mutant UDG polypeptide according to the present invention comprises an amino acid substitution at the position 57. In one embodiment, the lysine (K) residue at the 57th position of the wild type UDG is substituted with alanine (A) or glycine (G), which is similar to the alanine in size and chemical characteristics.

In one embodiment, Table 1 is a list of the mutant UDGs of the present invention and SEQ ID NOs thereof as well as wild-type UDG from *E. coli*.

TABLE 1

| SEQ ID NO | Name |
|---|---|
| 1 | WT UDG |
| 2 | E4A Substitution |
| 3 | W7A Substitution |
| 4 | E13A Substitution |
| 5 | Q16A Substitution |
| 6 | Y19A Substitution |
| 7 | D43A Substitution |
| 8 | D43C Substitution |
| 9 | D43G Substitution |
| 10 | D43H Substitution |
| 11 | D43I Substitution |
| 12 | D43K Substitution |
| 13 | D43P Substitution |
| 14 | D43R Substitution |
| 15 | D43V Substitution |
| 16 | D43W Substitution |
| 17 | F48A Substitution |
| 18 | F50A Substitution |
| 19 | E52A Substitution |
| 20 | K57A Substitution |
| 21 | I60A Substitution |
| 22 | H67A Substitution |
| 23 | Q71A Substitution |

TABLE 1-continued

| SEQ ID NO | Name |
|---|---|
| 24 | H73A Substitution |
| 25 | F77A Substitution |
| 26 | R80A Substitution |
| 27 | P87A Substitution |
| 28 | L96A Substitution |
| 29 | E97A Substitution |
| 30 | N107A Substitution |
| 31 | E112A Substitution |
| 32 | L121A Substitution |
| 33 | H134A Substitution |
| 34 | E142A Substitution |
| 35 | F144A Substitution |
| 36 | R156A Substitution |
| 37 | E157A Substitution |
| 38 | F161A Substitution |
| 39 | L162A Substitution |
| 40 | W164A Substitution |
| 41 | K171A Substitution |
| 42 | Q178A Substitution |
| 43 | R179A Substitution |
| 44 | H180A Substitution |
| 45 | L183A Substitution |
| 46 | H202A Substitution |
| 47 | G214E Substitution |
| 48 | G214R Substitution |
| 49 | G214W Substitution |
| 50 | E215A Substitution |
| 51 | W220A Substitution |
| 52 | L224A Substitution |
| 53 | D43X Substitution |

In another embodiment, the present mutant UDGs comprises two or more substitutions as a Combination.

In one embodiment, when two or more substitutions are included as a combination, the substitution at the position 43 is included in combination with K57A, E157A or E215A.

In one embodiment, D43A/K57A, D43A/E157A, D43A/E215A, D43A/K57A/E157A, D43A/E157A/E215A, or D43A/K57A/E157A/E215A are included in the present disclosure without being limited thereto.

However, the polypeptides according to the present invention are not limited to the sequences described herein, but include biological equivalents thereof. The term biological equivalents refer to polypeptides which contain additional modifications to the amino acid sequences disclosed herein, but have substantially the same or similar activity as the polypeptide disclosed herein.

In one embodiment, the mutant UDG polypeptides according to the present disclosure include the ones with conservative amino acid substitutions. Conservative amino acid substitution refers to a substitution that does not substantially affect or change or decrease the activity of a specific polypeptide.

The conservative amino acid substitutions are known in the related art, which may be referred to for example Table 2 based on Blosum (BLOcks SUbstitution Matrix): Creighton (1984) Proteins. W. H. Freeman and Company (Eds); Henikoff, S.; Henikoff, J. G. (1992). "Amino Acid Substitution Matrices from Protein Blocks". PNAS 89 (22): 10915-10919. doi:10.1073/pnas.89.22.10915; and WO2009012175 A1.

TABLE 2

| Original Residue | Very Highly - Conserved Substitutions | Highly Conserved Substitutions (from the Blosum90 Matrix) | Conserved Substitutions (from the Blosum65 Matrix) |
| --- | --- | --- | --- |
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Furthermore, when considering variants having biologically equivalent activities as described above, it is encompassed in the present invention not only the amino acid sequences disclosed herein or nucleic acids encoding the same as described below, also the sequences substantially identical to the sequences disclosed herein. The term "sequences substantially identical" refers to those showing preferably at least 61%, more preferably at least 70%, still more preferably at least 80%, most preferably at least 90% similarity to the sequence disclosed herein, when aligning sequences with the sequence disclosed herein so as to correspond to each other to the highest possible extent and analyzing the aligned sequences using algorithms that are generally used in the art. Methods of alignment of sequences for comparison are well-known in the art. Various programs and alignment algorithms are described in, for example, Smith and Waterman, *Adv. Appl. Math.* (1981) 2:482; Needleman and Wunsch, *J. Mol. Bio.* (1970) 48:443; Pearson and Lipman, Methods in *Mol. Biol.* (1988) 24: 307-31; Higgins and Sharp, Gene (1988) 73:237-44; Higgins and Sharp, *CABIOS* (1989) 5:151-3; Corpet et al., *Nuc. Acids Res.* (1988) 16:10881-90; Huang et al., *Comp. Appl. BioSci.* (1992) 8:155-65 and Pearson et al., *Meth. Mol. Biol.* (1994) 24:307-31. The NCBI Basic Local Alignment Search Tool (BLAST) (Altschul et al., *J. Mol. Biol.* (1990) 215:403-10) is available from the NBCI and the like, for use in connection with the sequence analysis programs such as blast, blastp, blasm, blastx, tblastn and tblastx. The BLAST can be accessed at ncbi.nlm.nih.gov/BLAST/. A description of how to determine sequence identity using this program is available at ncbi.nlm.nih.gov/BLAST/blast_help.html.

The mutant UDGs according to the present disclosure are used prior to the RT reaction, PCR or RT-PCR reaction, in particular to eliminate carryover contaminations of nucleic acids.

As used herein, the term RT (Reverse Transcription) is a reaction that synthesizes complementary DNA (cDNA) from mRNA. For this purpose, a reverse transcriptase is used, and the reactions are generally carried out at about 42 to 60° C. for about 30 minutes. Reverse transcriptase are commercially available. Since the cDNA synthesized in the reverse transcription reaction is used as a template for the PCR reactions, it is important to remove any contaminations from the RT reaction, and it is also important not to negatively affect the subsequent PCR reaction. In particular, the present UDGs may work advantageously in one-step RT-PCR performed in one test tube. In one embodiment of RT-PCR employing the UDG according to the present disclosure, the RT-PCR reaction mixture containing the present UDG is incubated at the temperature ranging from 15 to 55° C. for about 10 minutes, which is then followed by a RT reaction performed at the temperature ranging from about 42 to 60° C. for about 30 minutes, which is then followed by a PCR for example at the following condition: 1 cycle of denaturation at 92 to 95° C. for 0.5 minutes, and 25 to 40 cycles of annealing at 50~ 65° C. for ~ 1 minute and synthesis at 70~ 74° C. for ~ 1 minute/kb as one cycle. The conventional UDGs cannot be used for RT-PCR because the reaction temperature of the UDG and RT overlap. However, the UDGs according to the present disclosure is substantially inactivated at the temperature used for RT reaction (for example, 42° C.), and thus can be used advantageously in RT-PCR.

The term PCR (Polymerase Chain Reaction) as used herein is a method of amplifying a specific nucleic acid and is one of the most widely used methods in the fields of biology, biochemistry, and medicine (Yamamoto, Y. *Clin. Diagn. Lab. Immunol.* 2002, 9 (3), 508-514). In PCR, a cycle consisting of three steps of denaturation, primer binding and elongation is repeated many times and each step of the cycle is carried out at an optimal temperature for each step. The most widely used enzyme for PCR is Taq DNA polymerase derived from *Thermus aquaticus*, which enables efficient and stable PCR due to thermal stability at high temperatures. PCR includes both qualitative PCR to check the presence or absence of a specific nucleic acid, quantitative PCR to measure the amount of specific nucleic acid, and real-time PCR that enables qualitative and quantitative analysis by tracking the PCR process in real-time.

In another aspect, the present disclosure relates to a kit or composition comprising the mutant UDG protein according to the present disclosure, for removing nucleic acid contaminants in a reactant or reaction mixture for an RT, RT-PCR or PCR reaction.

Further in another aspect, the present disclosure relates to a kit or composition for RT, RT-PCR or PCR reaction comprising the mutant UDG protein according to the present disclosure.

The composition according to the present disclosure may be provided in the form of a premix. Premix is a composition in which the reagents required for a particular reaction are premixed for the user at the manufacturing process and supplied as a concentrated mixture. For example, the present UDGs may be employed for RT (Reverse Transcription, Reverse Transcription), PCR (Polymerase Chain Reaction), RT-PCR or quantitative PCR (qPCR), and the UDG of the present disclosure may be added to the existing premix for such reactions. For example, a PCR premix using the present UDG may comprise the present UDG, a heat-resistant polymerase, dNTPs, a buffer solution (buffer), and the user simply add template DNA, primers, and purified water before use. PCR premix may contain the present UDG, a Taq polymerase, divalent cations such as $Mg^{2+}$ or $Mn^{2+}$ dNTPs, salts, buffers, preservatives and/or additives. Among the above components, examples of the salts include KCl, NaCl, Ammonium sulfate, examples of the buffers include Tris-HCl, Sodium-/Potassium phosphate, examples of the preservatives include glycerol, examples of the additives include DMSO, but are not particularly limited thereto. Depending on the specific purpose or use, the composition according to the present disclosure may be mixed with other enzymes having particular desired activity, for example, such as Pfu DNA polymerase, dUTPase, Pyrophosphatase, Reverse Transcriptase, DNase/RNase Inhibitor, in which case, the composition may be modified or further comprise reagents required for the activity of the corresponding enzymes.

In another aspect, the present disclosure relates to a method of removing the nucleic acid contamination/contaminants in the reactions of RT (Reverse Transcription, Reverse Transcription), PCR (Polymerase Chain Reaction), RT-PCR, or quantitative PCR (qPCR) using the present UDG polypeptides.

The UDGs according to the present disclosure have an optimal reaction temperature and inactivation temperature of about 5 to 10° C. lower than that of the wild type. Thus, the present UDGs can be advantageously used in one-step RT-PCR/RT-qPCR in which a RT generally carried out at 42 to 50° C. is combined with PCR. In addition, the present UDGs can also be advantageously used in a PCR in which a melting and amplification steps are combined and carried out in one-step at relatively low temperatures.

In one embodiment of the method according to the present disclosure, the nucleic acid de-contamination reaction using the UDG according to the present disclosure may be carried out at the temperature ranging from 15° C. to 55° C., or 35 to 45° C., in particular at 40° C.

The mutant UDGs according to the present disclosure can be effectively inactivated during RT reactions. The RT reactions generally are carried out at 42° C., and occasionally at a temperature up to 60° C. In particular, the activity of the present UDGs D43A, D43C, D43H, D43R, D43V, and D43W is lost by 100% at 45° C. (FIG. 20) and start to get inactivated before the RT reaction starting at 42° C. Thus the present mutant UDGs do not cleave the cDNA synthesized in RT reaction and thus can be advantageously applicable in RT-PCR.

The mutant UDGs according to the present disclosure are inactivated at the temperature used for PCR. PCR requires a specific temperature for each step of denaturation/primer annealing/elongation. Especially in the case of Multiplex Realtime PCR using multiple sets of primers, due to the limitations in the TaqMan® probe sequence design, it is sometimes necessary to perform an annealing reaction at a relatively low temperature (about 50° C. or less). In such cases, when E. coli-derived UDG enzymes are used, it significantly lowers the amplification efficiency of the PCR because the conventional UDGs have the activity at the annealing temperature and retain the activity even after the heat treatment (initial denaturation temperature). The UDGs according to the present disclosure can be advantageously used together with PCR employing an annealing step at about 50° C. or less as described in FIG. 14 herein.

In one embodiment, the PCR methods using the UDGs according to the present disclosure may be used in a PCR reaction employing an annealing step performed at about 50° C. or less, for example, about 45° C. to about 50° C. It can also be useful for two-step PCR, where annealing and DNA synthesis steps are performed in one step.

In one embodiment, the present UDGs are used before the start of the PCR reaction to remove the nucleic acid contamination which may be present in the samples/reactants/mixtures. For example, the PCR reaction mixtures or the templates or the samples are treated with the UDG according to the present disclosure for about 10 minutes at about 15~55° C. to remove the contaminants, which is then followed by an incubation at about 92~95° C. for about 0.5 minutes (denaturation) for inactivating the UDGs and at the same time for denaturing the template at the start of the PCR reaction which is performed for example for 25-40 cycles of about 0.5 minutes (denaturation) at about 92~95° C.; about 1 minute (annealing) at about 50-65° C. and about 1 minute/kb (synthesis) at about 70-74° C.

In other embodiment, the present UDGs are used in one-step RT-PCR, and the sample/reactants/mixtures are treated with UDG at about 15 to 55° C. for about 10 minutes to remove nucleic acid contamination/contaminants from the sample/reactants, which is followed by an incubation at about 42 to 60° C. for about 30 minutes for RT reaction. The UDGs according to the present invention are substantially inactivated in such RT temperature and thus can be advantageously used for one-step RT-PCR. The RT is then followed by PCR in the same tube performed for example for 25-40 cycles of about 0.5 minutes (denaturation) at about 92~95° C.; about 1 minute (annealing) at about 50-65° C. and about 1 minute/kb (synthesis) at about 70-74° C.

In other embodiment, the separate incubation step with UDG may be omitted in RT or RT-PCR reactions. For example, a UDG reaction may occur at room temperature while preparing the premix for the corresponding reaction at room temperature. And the present UDG in the premix is effectively inactivated in the subsequent reactions.

In other aspect, the present disclosure also relates to a polynucleotide encoding the UDGs according to the present disclosure described herein, a recombinant vector comprising the polynucleotide, and a cell into which the recombinant vector has been introduced. The polynucleotide sequence can be easily determined from a known codon sequence encoding each of 20 amino acids when the protein sequence is disclosed. When there are a plurality of codons encoding the same amino acid, the skilled person in the related art can select without difficulty the type of codon that is preferentially used in the species of interest which are known in the art. Here, a polynucleotide sequence can be determined using a codon preferentially used in E. coli.

The polynucleotides according to the present disclosure may be introduced into suitable vectors which may be used for various purposes, such as protein production. For example, to be able to express the protein of interest in a suitable host, the present polynucleotide sequence may be operatively linked to a suitable regulatory sequence, such as a promoter capable of initiating transcription, an operator sequence for regulating such transcription, a sequence encoding a suitable mRNA ribosome binding site, or a sequence that controls the termination for transcription and translation. The vectors or plasmids into which the polynucleotide according to the present disclosure can be introduced are not particularly limited as long as it is replicable in a host cell of interest. Any known vectors may be used according to a specific purpose including natural or recombinant plasmids, phagemid, cosmid, virus vectors, and bacteriophage. Forexample, pWE15, M13, λMBL3, λMBL4, λIXII, λASHII, λAPII, λt10, λt11, Charon4A, and Charon21A may be used as a phage vectors or cosmid vectors, and as a plasmid vectors, pBR system, pUC system, pBluescript® II system, pGEM-based, pTZ-based, pCL-based, and pET-based vectors, such as pACYC177, pACYC184, pCL, pECCG117, pUC19, pBR322, pMW118, pC1BAC, pET-21a, pET-32a vectors, and the like may be used.

A vector comprising a polynucleotide according to the present application can be used for various purpose by introducing the vector into a suitable host cell. The vector may replicate or function independently of the host genome, and may be integrated into the genome of the host cell.

The cells comprising a polynucleotide according to the present application or a vector comprising the same include prokaryotic cells in particular. For example, it includes, but is not particularly limited to, bacterial cells such as *Escherichia coli*, *Streptomyces*, and *Salmonella typhimurium*.

The polynucleotide according to the present application includes DNA and RNA, and may be introduced into a host cell in various forms for expression. For example, the polynucleotide may be introduced into a host cell in the form of an expression cassette, which is a gene construct including all elements necessary for self-expression. The expression cassette usually includes a promoter operably linked to the polynucleotide, a transcription termination signal, a ribosome binding site, and a translation termination signal. The expression cassette may be in the form of an expression vector capable of self-replicating. In addition, the polynucleotide may be introduced into a host cell in its own form and operably linked to a sequence required for expression in the host cell.

In other aspect, the present application also provides a method for producing a mutant UDG proteins according to the present disclosure comprising the steps of culturing the recombinant cells to obtain a culture and recovering the polypeptides from the cultured cells or culture.

In the present invention, the step of culturing the recombinant cells is not particularly limited thereto, but is preferably performed by a known batch culture method, a continuous culture method, a fed-batch culture method, and the like. The culture conditions are not particularly limited thereto, and may be carried out as following conditions: growth at pH 5 to 9, preferably pH 6 to 8, most preferably pH 6.8 titrated using basic compound (e.g. sodium hydroxide, potassium hydroxide, or ammonia) or an acidic compound (e.g. phosphoric acid or sulfuric acid); oxygen or oxygen-containing gas mixture may be introduced into the culture to maintain aerobic conditions; the culture may be performed at the temperature of about 20 to 45° C., preferably 25 to 40° C., for about 10 to 160 hours. The polypeptides produced by the present methods may be secreted into the medium or may remain in the cells.

In the present invention, the culture medium employed may include as a carbon source sugars and carbohydrates (e.g. glucose, sucrose, lactose, fructose, maltose, molasse, starch and cellulose), fats and lipids (e.g. soybean oil, Sunflower seed oil, peanut oil and coconut oil), fatty acids (e.g. palmitic acid, stearic acid and linoleic acid), alcohols (e.g. glycerol and ethanol) and organic acids (e.g. acetic acid), which may be used alone or in combination; as a nitrogen sources nitrogen-containing organic compounds (e.g., peptone, yeast extract, broth, malt extract, corn steep liquid, soybean meal and urea), or inorganic compounds (e.g. ammonium sulfate, ammonium chloride, ammonium phosphate, ammonium carbonate, and Ammonium nitrate) and the like, which may be used alone or in combination; and as a phosphorus source, potassium dihydrogen phosphate, dipotassium hydrogen phosphate, corresponding sodium-containing salts and the like, which may be used alone or in combination; and other metal salts (e.g. magnesium sulfate or iron sulfate), amino acids and essential growth-promoting substances such as vitamins.

The step of recovering the polypeptides produced in the culturing step of the present invention may be performed using a suitable method known in the art depending on the particular culture method employed, for example, a batch, continuous, or fed-batch culture method.

The present invention can be practiced using conventional methods within the technical level of molecular biology and DNA recombination technologies unless otherwise stated. In addition, the following books and documents may be referred to for more detailed descriptions of general techniques. For general methods of molecular biology and biochemistry, *Molecular Cloning: A Laboratory Manual*, 3rd Ed. (Sambrook et al., Cold Spring Harbor Laboratory Press 2001); Short Protocols in Molecular Biology, 4th Ed. (Ausubel et al. eds., John Wiley & Sons 1999); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); *Current Protocols in Molecular Biology* and Short Protocols in Molecular Biology, 3rd Edition (Ausubel et al., eds.); and Recombinant DNA Methodology (Wu, ed., Academic Press) and the like may be referred.

The present disclosure is further explained in more detail with reference to the following examples. These examples, however, should not be interpreted as limiting the scope of the present invention in any manner.

EXAMPLES

Example 1. Screening of Thermosensitive Amino Acid Residues Through UDG Structure Analysis Molecular dynamics simulation was performed using supercomputing for the three-dimensional structure of the UDG protein derived from *E. coli* (PDB code: 2EUG) revealed by XRD experiments. Molecular dynamics simulation is a simulation that calculates the force between all atoms constituting a protein by differentiating a given force field with respect to distance, and describes the motion of a molecule using Newton's law ($F=ma=-dU/dx$). Using the AMBER force-field, a set of structures of a protein at a given temperature was obtained by molecular dynamics simulation, and all interaction energies between amino acid residues constituting the protein, that is, an energy network, were calculated.

FIG. 1 shows an energy network between amino acid residues extracted from the simulation, and Laplacian network clustering analysis was performed on this to obtain a hub of an energy network, and a list of amino acids important for structural stability was selected as follows: E13, Q16, D43, F50, K57, I60, E97, N107, H134, E142, R156, E157, L162, W164, K171, Q178, R179, H180, L183, H202, E215, W220, L224. In Laplacian network clustering assigns a weight if i,j are connected in a given network. Otherwise, it is the sum of the adjacency matrix (Aij) having a value of 0, and the weight of the diagonal components i,i of the matrix which are connected to node I, and the Degree Matrix(Dij) is obtained in which the remaining non-diagonal components are all 0. And it is defined as the Laplacian matrix Lij=Dij-Aij. And clustering is performed using the properties of the Laplacian matrix and the hub is obtained (By diagonalizing Lij, the components with the same value of the eigenvector corresponding to the nonzero lowest eigenvalue represent a group, and the components with the larger values of the eigenvector corresponding to a few largest eigenvalues are defined as hubs).

Example 2. Cloning of Thermal Sensitive Mutant UDG Candidates and Expression Thereof The UDG genes in which the residues selected in Example 1 were each substituted with alanine and cloned into a plasmid as follows. To this end, point mutations were artificially introduced into the selected residues of the wild-type *E. coli* UDG gene (SEQ ID NO: 2) using the EZchange™ Site-directed Mutagenesis Kit (Enzynomics, Korea) according to the manufacturer's instruction and the primers listed in Table 3. It was confirmed by sequencing that the correct mutation was introduced (GENOTECH, Daejeon, Korea and BIONICS, Seoul, Korea).

TABLE 3

Wild-type UDG nucleic acid sequence, Primer sets used for the construction and analysis of the mutant UDGs of the present disclosure and the substrates sequence used for the analysis of the mutants

| Name | | Nucleic Acid Sequence (5'→3') | SEQ ID NO |
|---|---|---|---|
| WT UDG | | atggctaacg aattaacctg gcatgacgtg ctggctgaag agaagcagca accctatttt cttaatacccc ttcagaccgt cgccagcgag cggcagtccg gcgtcactat ctacccacca caaaaagatg tctttaacgc gttccgcttt acagagttgg gtgacgttaa agtggtgatt ctcggccagg atccttatca cggaccggga caggcgcatg gtctggcatt ttccgttcgt cccggcattg ccattcctcc gtcattattg aatatgtata aagagctgga aaatactatt ccgggcttca cccgccctaa tcatggttat cttgaaagct gggcgcgtca gggcgttctg ctactcaata ctgtgttgac ggtacgcgca ggtcaggcgc attcccacgc cagcctcggc tgggaaacct tcaccgataa agtgatcagc ctgattaacc agcatcgcga aggcgtggtg ttttgttgt ggggatcgca tgcgcaaaag aaagggggcga ttatagataa gcaacgccat catgtactga aagcaccgca tccgtcgccg ctttcggcgc atcgtggatt ctttggctgc aaccattttg tgctggcaaa tcagtggctg gaacaacgtg gcgagacgcc gattgactgg atgccagtat taccggcaga gagtgagtaa | 54 |
| E4A | Forward | 5'-GCATTAACCTGGCATGACGTGCTGGCTGAAG | 55 |
| | Reverse | 5'-GTTAGCCATGCCACCAATCTGTTCTCTGTGAGCC | 56 |
| W7A | Forward | 5'-GCGCATGACGTGCTGGCTGAAGAGAAG | 57 |
| | Reverse | 5'-GGTTAATTCGTTAGCCATCCCACCAATCTGTTCTC | 58 |
| E13A | Forward | 5'-GCAGAGAAGCAGCAACCCTATTTTCTTAATACCCT | 59 |
| | Reverse | 5'-AGCCAGCACGTCATGCCAGGTTAATT | 60 |
| Q16A | Forward | 5'-GCGCAACCCTATTTTCTTAATACCCTTCAGACCG | 61 |
| | Reverse | 5'-CTTCTCTTCAGCCAGCACGTCATGCC | 62 |
| Y19A | Forward | 5'-GCTTTTCTTAATACCCTTCAGACCGTCGCCAG | 63 |
| | Reverse | 5'-GGGTTGCTGCTTCTCTTCAGCCAGCAC | 64 |
| D43A | Forward | 5'-GCTGTCTTTAACGCGTTCCGCTTTACAGAG | 65 |
| | Reverse | 5'-TTTTTGTGGTGGGTAGATAGTGACGCC | 66 |
| D43C | Forward | 5'-TGTGTCTTTAACGCGTTCCGCTTTACAGAG | 67 |
| | Reverse | 5'-TTTTTGTGGTGGGTAGATAGTGACGCCG | 68 |
| D43G | Forward | 5'-GGTGTCTTTAACGCGTTCCGCTTTACAGAG | 69 |
| | Reverse | 5'-TTTTTGTGGTGGGTAGATAGTGACGCCG | 70 |
| D43H | Forward | 5'-CATGTCTTTAACGCGTTCCGCTTTACAGAG | 71 |
| | Reverse | 5'-TTTTTGTGGTGGGTAGATAGTGACGCCG | 72 |
| D43I | Forward | 5'-ATTGTCTTTAACGCGTTCCGCTTTACAGAG | 73 |
| | Reverse | 5'-TTTTTGTGGTGGGTAGATAGTGACGCCG | 74 |
| D43K | Forward | 5'-AAGGTCTTTAACGCGTTCCGCTTTACAGAG | 75 |
| | Reverse | 5'-TTTTTGTGGTGGGTAGATAGTGACGCCG | 76 |
| D43P | Forward | 5'-CCTGTCTTTAACGCGTTCCGCTTTACAGAG | 77 |
| | Reverse | 5'-TTTTTGTGGTGGGTAGATAGTGACGCCG | 78 |

TABLE 3-continued

Wild-type UDG nucleic acid sequence, Primer sets used for the construction and analysis of the mutant UDGs of the present disclosure and the substrates sequence used for the analysis of the mutants

| Name | | Nucleic Acid Sequence (5'→3') | SEQ ID NO |
|---|---|---|---|
| D43R | Forward | 5'-CGTGTCTTTAACGCGTTCCGCTTTACAGAGTTGGGTG | 79 |
| | Reverse | 5'-TTTTTGTGGTGGGTAGATAGTGACGCCGGACTGCC | 80 |
| D43V | Forward | 5'-GTTGTCTTTAACGCGTTCCGCTTTACAGAG | 81 |
| | Reverse | 5'-TTTTTGTGGTGGGTAGATAGTGACGCCG | 82 |
| D43W | Forward | 5'-TGGGTCTTTAACGCGTTCCGCTTTACAGAG | 83 |
| | Reverse | 5'-TTTTTGTGGTGGGTAGATAGTGACGCCG | 84 |
| F48A | Forward | 5'-GCCCGCTTTACAGAGTTGGGTGACGTTAAAGTG | 85 |
| | Reverse | 5'-CGCGTTAAAGACATCTTTTTGTGGTGGGTAGATAGTG | 86 |
| F50A | Forward | 5'-GCTACAGAGTTGGGTGACGTTAAAGTGGTG | 87 |
| | Reverse | 5'-GCGGAACGCGTTAAAGACATCTTTT | 88 |
| E52A | Forward | 5'-GCGTTGGGTGACGTTAAAGTGGTGATTCTCG | 89 |
| | Reverse | 5'-TGTAAAGCGGAACGCGTTAAAGACATCTTTTTGTG | 90 |
| K57A | Forward | 5'-GCAGTGGTGATTCTCGGCCAGGATCCTT | 91 |
| | Reverse | 5'-AACGTCACCCAACTCTGTAAAGCGG | 92 |
| I60A | Forward | 5'-GCTCTCGGCCAGGATCCTTATCACGG | 93 |
| | Reverse | 5'-CACCACTTTAACGTCACCCAACTCTGTAAAGC | 94 |
| H67A | Forward | 5'-GCCGGACCGGGACAGGCGCATGGTCTG | 95 |
| | Reverse | 5'-ATAAGGATCCTGGCCGAGAATCACCACTTTAACGTCACC | 96 |
| Q71A | Forward | 5'-GCGGCGCATGGTCTGGCATTTTCCGTTCG | 97 |
| | Reverse | 5'-TCCCGGTCCGTGATAAGGATCCTGGCCGAGAATC | 98 |
| H73A | Forward | 5'-GCTGGTCTGGCATTTTCCGTTCGTCCCG | 99 |
| | Reverse | 5'-CGCCTGTCCCGGTCCGTGATAAGGATCCTG | 100 |
| F77A | Forward | 5'-GCTTCCGTTCGTCCCGGCATTGCCATTCC | 101 |
| | Reverse | 5'-TGCCAGACCATGCGCCTGTCCCGGTCC | 102 |
| R80A | Forward | 5'-GCTCCCGGCATTGCCATTCCTCCGTC | 103 |
| | Reverse | 5'-AACGGAAAATGCCAGACCATGCGCCTGTC | 104 |
| P87A | Forward | 5'-GCGTCATTATTGAATATGTATAAAGAGCTGGAAAATACTATTC | 105 |
| | Reverse | 5'-AGGAATGGCAATGCCGGGACGAAC | 106 |
| L96A | Forward | 5'-GCGGAAAATACTATTCCGGGCTTCACCCG | 107 |
| | Reverse | 5'-CTCTTTATACATATTCAATAATGACGGAGGAATGGCAATGC | 108 |
| E97A | Forward | 5'-GCAAATACTATTCCGGGCTTCACCCGC | 109 |
| | Reverse | 5'-CAGCTCTTTATACATATTCAATAATGACGGAGGAA | 110 |
| N107A | Forward | 5'-GCTCATGGTTATCTTGAAAGCTGGGCGCG | 111 |
| | Reverse | 5'-AGGGCGGGTGAAGCCCGGAATAGTAT | 112 |
| E112A | Forward | 5'-GCAAGCTGGGCGCGTCAGGGCGTTC | 113 |
| | Reverse | 5'-AAGATAACCATGATTAGGGCGGGTGAAGCCCGG | 114 |
| L121A | Forward | 5'-GCACTCAATACTGTGTTGACGGTACGCGCAGGTC | 115 |
| | Reverse | 5'-CAGAACGCCCTGACGCGCCCAGCTTTC | 116 |
| H134A | Forward | 5'-GCTTCCCACGCCAGCCTCGGCTGGG | 117 |
| | Reverse | 5'-CGCCTGACCTGCGCGTACCGTCAACACAG | 118 |
| E142A | Forward | 5'-GCAACCTTCACCGATAAAGTGATCAGCCTGATTAAC | 119 |
| | Reverse | 5'-CCAGCCGAGGCTGGCGTGGG | 120 |
| F144A | Forward | 5'-GCCACCGATAAAGTGATCAGCCTGATTAACCAGCATC | 121 |
| | Reverse | 5'-GGTTTCCCAGCCGAGGCTGGCGTGG | 122 |
| R156A | Forward | 5'-GCCGAAGGCGTGGTGTTTTTGTTGTGG | 123 |
| | Reverse | 5'-ATGCTGGTTAATCAGGCTGATCACTTTATC | 124 |
| E157A | Forward | 5'-GCAGGCGTGGTGTTTTTGTTGTGGGGAT | 125 |
| | Reverse | 5'-GCGATGCTGGTTAATCAGGCTGATCACTTT | 126 |

TABLE 3-continued

Wild-type UDG nucleic acid sequence, Primer sets used for the construction and analysis of the mutant UDGs of the present disclosure and the substrates sequence used for the analysis of the mutants

| Name | | Nucleic Acid Sequence (5'→3') | SEQ ID NO |
|---|---|---|---|
| F161A | Forward | 5'-GCTTTGTTGTGGGGATCGCATGCGCAAAAG | 127 |
| | Reverse | 5'-CACCACGCCTTCGCGATGCTGGTTAATCAG | 128 |
| L162A | Forward | 5'-GCGTTGTGGGGATCGCATGCGCAAA | 129 |
| | Reverse | 5'-AAACACCACGCCTTCGCGATGCTGGT | 130 |
| W164A | Forward | 5'-GCGGGATCGCATGCGCAAAAGAAAGG | 131 |
| | Reverse | 5'-CAACAAAAACACCACGCCTTCGCGA | 132 |
| K171A | Forward | 5'-GCAGGGGCGATTATAGATAAGCAACGCCATC | 133 |
| | Reverse | 5'-CTTTTGCGCATGCGATCCCCACAAC | 134 |
| Q178A | Forward | 5'-GCACGCCATCATGTACTGAAAGCACCG | 135 |
| | Reverse | 5'-CTTATCTATAATCGCCCCTTTCTTTTGCGC | 136 |
| R179A | Forward | 5'-GCCCATCATGTACTGAAAGCACCGCATCC | 137 |
| | Reverse | 5'-TTGCTTATCTATAATCGCCCCTTTCTTTTGC | 138 |
| H180A | Forward | 5'-GCTCATGTACTGAAAGCACCGCATCCG | 139 |
| | Reverse | 5'-GCGTTGCTTATCTATAATCGCCCCTTTC | 140 |
| L183A | Forward | 5'-GCGAAAGCACCGCATCCGTCGCCGCTTT | 141 |
| | Reverse | 5'-TACATGATGGCGTTGCTTATCTATAATCGCCCCTTTC | 142 |
| H202A | Forward | 5'-GCTTTTGTGCTGGCAAATCAGTGGCTG | 143 |
| | Reverse | 5'-GTTGCAGCCAAAGAATCCACGATGC | 144 |
| G214E | Forward | 5'-GAGGAGACGCCGATTGACTGGATGCCAGTATTACCG | 145 |
| | Reverse | 5'-ACGTTGTTCCAGCCACTGATTTGCCAGCACAAATG | 146 |
| G214R | Forward | 5'-CGCGAGACGCCGATTGACTGGATGCCAG | 147 |
| | Reverse | 5'-ACGTTGTTCCAGCCACTGATTTGCCAGCACAAATG | 148 |
| G214W | Forward | 5'-TGGGAGACGCCGATTGACTGGATGCCAGTATTACC | 149 |
| | Reverse | 5'-ACGTTGTTCCAGCCACTGATTTGCCAGCACAAATG | 150 |
| E215A | Forward | 5'-GCGACGCCGATTGACTGGATGCCAGTAT | 151 |
| | Reverse | 5'-GCCACGTTGTTCCAGCCACTGATTTG | 152 |
| W220A | Forward | 5'-GCGATGCCAGTATTACCGGCAGAGAGTGAG | 153 |
| | Reverse | 5'-GTCAATCGGCGTCTCGCCACGT | 154 |
| L224A | Forward | 5'-GCACCGGCAGAGAGTGAGTAAATGGCTAACG | 155 |
| | Reverse | 5'-TACTGGCATCCAGTCAATCGGCGTC | 156 |
| GAPDH | Forward | 5'-ACGGATTTGGTCGTATTGGGC-3' | 157 |
| | Reverse | 5'-TTGACGGTGCCATGGAATTTG-3' | 158 |
| | Probe | 5'-CCTGGTCACCAGGGCTGC TTTTAA-3' | 159 |
| | Substrate 1 | 5'-GGA ACA ATT CUG CGG CTT TAG-3' | 160 |
| | Substrate 2 | 5'-CTA AAG CCG CAG AAT TGT TCC-3 | 161 |

Then, the 24 mutant UDGs prepared as described above were expressed as follows. The expression vectors containing each of the 24 thermal sensitive UDG candidate genes were transformed by calcium chloride heat shock into BL21 (DE3)RIL strains, respectively. Subsequently, the transformed single *E. coli* colony was incubated at 37° C. until OD600 is 0.5-1, and then 1 mM IPTG was added and cultured for 4 hours to express the proteins. Subsequently, a cell pellet was obtained through centrifugation, the cells were disrupted by sonication, and then centrifuged again to analyze the soluble fraction and the insoluble fraction by SDS-PAGE method. As a result, it is confirmed that the target protein was expressed in a total of 25 samples including wild-type as shown in FIG. 2A to 2F.

Example 3. Measurement of Thermal Sensitivity of the Present UDG Mutants

Subsequently, in vitro UDG activity assays were performed to select the mutants with increased thermal sensitivity among the 24 UDG mutant proteins expressed in Example 2. This is an experimental method in which a fully complementary double-stranded DNA labelled with a FAM fluorescent substance at the 5' end and containing one dU in the middle is used as a substrate (see FIGS. 3 and 4).

Figure 3:
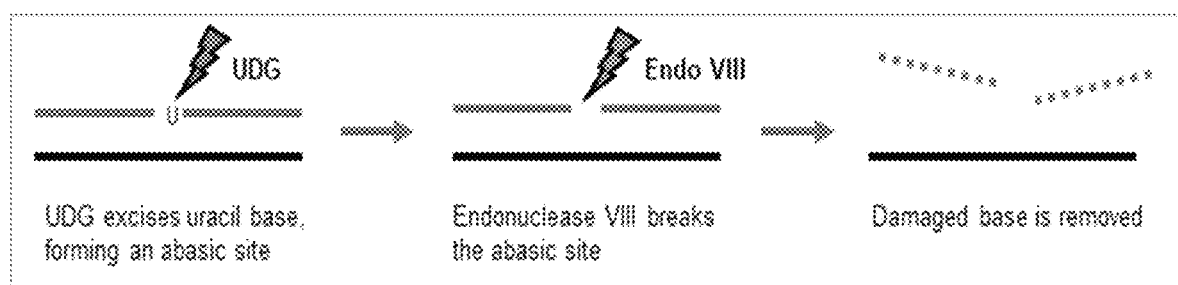
FIG. 3 is a schematic representation of the principle of in vitro UDG activity assay, which is used in the present invention to test the thermal sensitivity of the mutant UDGs prepared in accordance with the present invention.
Figure 4:
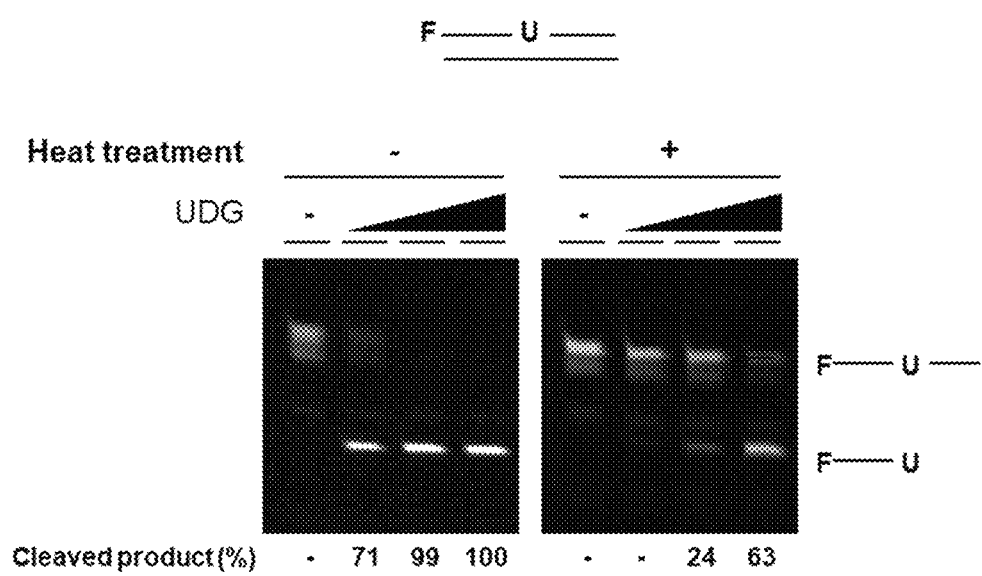
FIG. 4 is the result of denaturing PAGE of the analytes from the assay as depicted in FIG. 3 showing that specific analysis of the cleaved single strand is possible.

To this end, a total of 20 µl of the reaction mixture was prepared by mixing 10× USE Reaction Buffer (EZ™ USE Enzyme, Enzynomics, Korea), 100 ng of Endonuclease VIII (Enzynomics), and 20 pmol of a double-stranded fluorescent dU substrate. Here, wild-type or mutant UDG with or without heat treatment at 95° C. for 5-15 minutes was added to the reaction mixture and incubated at 37° C. for 15 minutes to allow the formation of an abasic site by removing the uracil base of dU by UDG. Then the abasic sites are cleaved by an excessive amount of Endonuclease VIII, and one strand of the double-stranded DNA is cleaved in proportion to the activity of the added UDG (FIG. 3). Then when the reaction mixture is analyzed by denaturing PAGE analysis, only the cleaved single strand can be specifically analyzed (FIG. 4).

Thermal sensitivity tests were performed on the 23 candidates mutant UDGs and wild-type UDG excluding the mutant clones producing insoluble protein by the in vitro UDG activity analysis method as described above. In the analysis, only the expressed soluble fractions were used after the quantification without the purification.

The rate of increase in the thermal sensitivity was calculated by the following formula: [The amount of enzyme required to cleave 50% substrates after the heat treatment]/ [The amount of enzyme required to cleave 50% substrates before the heat treatment]

Figure 5:
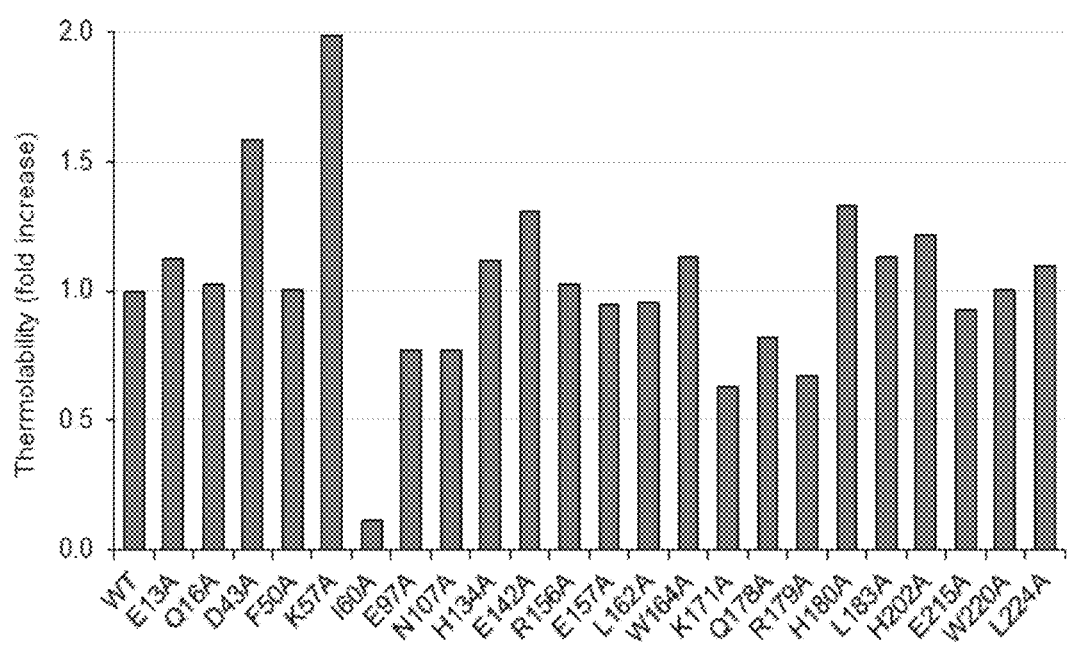
FIG. 5 is the result of the experiments performed according to FIGS. 3 and 4, to test the thermal sensitivity of the mutant UDGs prepared in accordance with one embodiment of the present invention.

The results are shown in FIG. 5. As shown there, it was confirmed that the D43A and K57A mutations increased thermal sensitivity by 50% or more compared to the wild type, respectively, and H134A, E142A, W164A, H180A, L183A, H202A, and L224A also increased the thermal sensitivity by 10% or more compared to the wild type. The specific activity of each UDG mutant was measured to be within 50% of the wild type except for the W164A clone, which indicates that the present mutants are suitable for PCR applications (Data not shown).

Example 4. Purification of the Mutant UDG and Measurement of Thermal

Sensitivity Thereof (1) Purification

For further development and evaluations, a total of five proteins, i.e., D43A and K57A mutants that showed an increase in thermal sensitivity by 50% or more based on the heat sensitivity evaluation experiment using in vitro UDG activity assay, and E157A and E215A mutants that showed to have a thermal sensitivity similar to that of wild type, and wild-type UDG were purified.

About 50 mg of soluble extracts containing the expressed UDG was mixed with 1 ml of Ni-NTA resin (Qiagen) and rotated overhead at 4° C. for 3 hours to induce binding of UDG and Ni-NTA resin. After transferring the mixture to the gravity column (Bio-rad), 20 column volume of W1 buffer (CB2000+5 mM IDZ), 20 column volume of W2 (DW), 10 column volume of W3 (2M NaCl+40% Ethylene glycol), 10 column volume of W4 buffer (CB300+20 mM IDZ) was sequentially used for washing. Finally, proteins were eluted using a W4 buffer containing 60 mM IDZ and an elution buffer containing 250 mM IDZ.

Through this, a total of five UDG enzymes, including wild-type UDG and four mutant UDGs, were purified. Maximum concentrations of up to 1.37 mg/ml (137,000 unit/ml) for wild-type UDG, up to 1.51 mg/ml (151,000 unit/ml) for D43A, up to 2.32 mg/ml (232,000 unit/ml) for K57A, up to 1.67 mg/ml (167,000 unit/ml) for E157A and up to 1.63 mg/ml (163,000 unit/ml) for E215A were obtained. The average purity of the obtained UDGs were confirmed to be in the range of about 90 to 95% as a result of the SDS-PAGE experiment.

(2) Measurement of Thermal Sensitivity Using In Vitro UDG Activity Assay.

Figure 6:
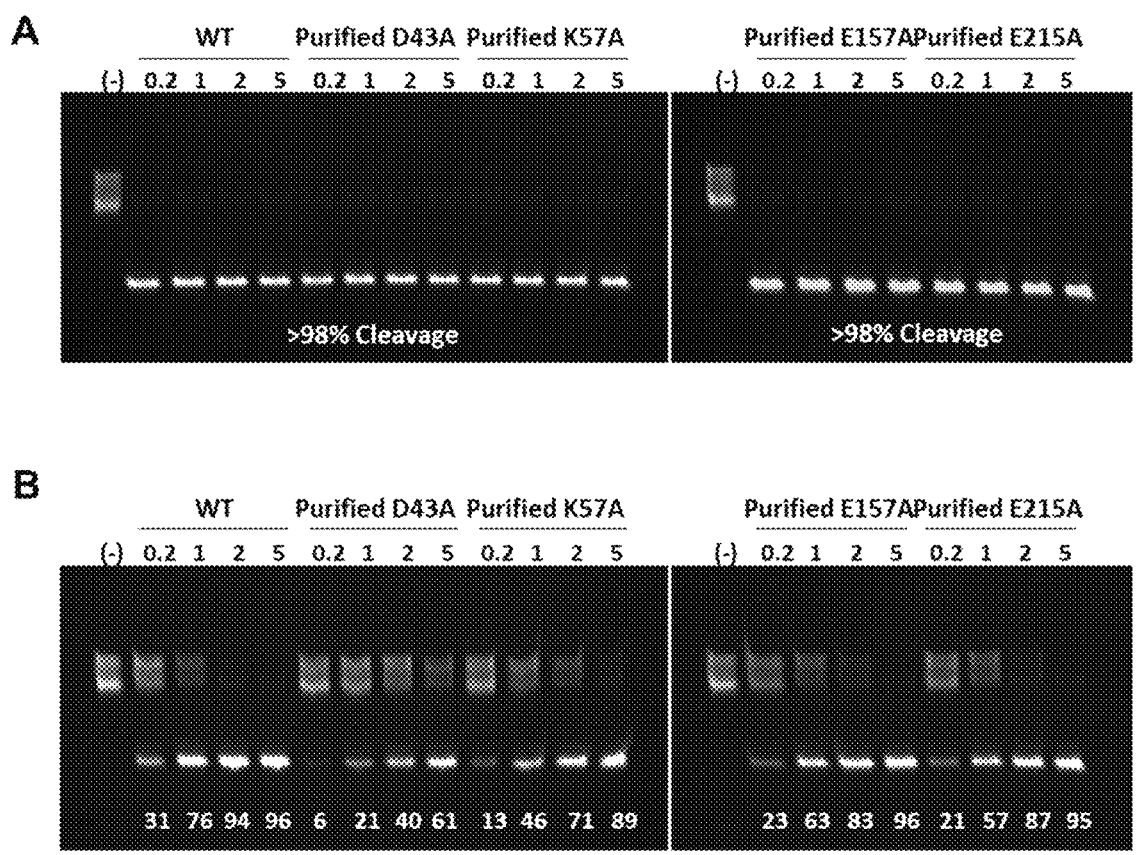
FIG. 6 is the result of the experiments performed according to FIGS. 3 and 4, to test the thermal sensitivity of the mutant UDG D43A, K57A, E157A and E215A selected as in FIG. 5. The D43A and K57A clones lost 3 to 5 times more activity than that of the wild-type UDG (at 0.2ng). In case of E157A and E215A, the decrease in activity by heat was about 30% greater than that of the wild type.

In order to more accurately measure the thermal sensitivity of the candidate mutant UDGs, an in vitro UDG activity assay was performed using the purified mutant UDGs as described above. The experiments were conducted in the same manner as in FIGS. 3 and 4 and the amount of UDG added was increased in the order of 0.2, 1, 2, 5 ng. The results are shown in FIG. 6. As shown therein, before the heat treatment, it was confirmed that the substrate included in the reaction mixture was cleaved by more than 98% between 0.2 ng and 1 ng regardless of wild type and mutant UDG used. However, when the heat treatment process was first performed at 95° C. for 15 minutes, it was confirmed that the D43A and K57A clones lost about 3 to 5 times more activity than the wild type (at 0.2 ng). In the case of E157A and E215A mutants, it was observed that the decrease in activity by heat was approximately about 30% greater than that of the wild type (at 0.2 ng).

(3) Thermal Sensitivity Measurement Using Radioactive Isotopes

In order to more directly confirm the increase in thermal sensitivity of the mutant UDGs, an activity measurement experiment using radioactive isotopes was performed. First of all, substrates labeled with a radioactive isotope were prepared. The sequence of DNA used for the substrate preparation is as follows. Substrate 1: 5'-GGA ACA ATT CUG CGG CTT TAG-3' (SEQ ID NO: 160), substrate 2:5'-CTA AAG CCG CAG AAT TGT TCC-3' (SEQ ID NO: 161). First, 20 pmol of substrate 1 oligonucleotide was labeled using 8.25 pmol of [γ-$^{32}$P] ATP and polynucleotide kinase (Enzynomics). After stopping the reaction by adding EDTA, 20 pmol of the substrate 2 oligonucleotide was added. The substrate solution was mixed in the final 1× Annealing buffer [125 mM NaCl, 25 mM Tris-HCl (pH 7.5)], and the two single-stranded DNAs were allowed to hybridize to form a double-stranded DNA in a PCR machine. Finally, it was purified through electrophoresis in 10% SDS-PAGE and gel purification.

The prepared substrates were used to evaluate the activity of wild-type and mutant UDGs before and after heat treatment. First, 200 fmol/μl of the purified wild-type and D43A mutant enzymes were heat-treated at 95° C. for 0, 2, 5, 10, and 20 minutes. Thereafter, 1 μl of each of these was used to react with 15 fmol of the substrate (20 mM Tris-HCl (pH 7.8), 0.1 mM DTT, 1 mM EDTA) in a total of 20 μl of the reaction solution. The reaction was carried out at 25° C. for 10 minutes, after which the reaction was stopped by adding the same volume of 2× stop solution. The reactants were treated in boiling water for 20 minutes, and then 2 μl of 3M HCl was added to neutralize the salt concentration. Finally, 8 μl of the reactants was separated by electrophoresis in 15% denaturing gel in 1× TBE at 35W for 30 minutes. The final electrophoresis gel was dried in a vacuum on 3MM (Whatman) paper at 85° C. for 2.5 hours and then analyzed using Phosphoimager and X-ray film.

Figure 7:
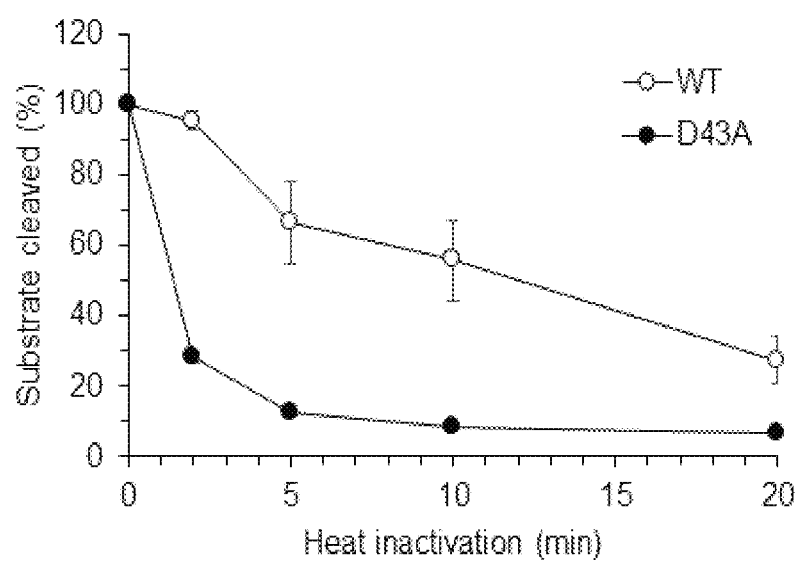
FIG. 7 is the result of the experiment to measure the thermal sensitivity of D43A mutant using an isotope. In case of the wild-type, it took about 15 minutes for the activity to be reduced by about 50%. However, in case of the present D43A clone, it was confirmed that the activity was decreased by at least 70% during the first 2 minutes of the heat treatment and by at least 90% by 5 minutes of the heat treatment. Through these results, it can be confirmed that the heat sensitivity of the mutant UDG is significantly higher than that of the wild type.

The results are shown in FIG. 7. As shown therein, in the case of the wild type, it took nearly 15 minutes to decrease the activity by about 50%, but in the case of the D43A clone, it was confirmed that the activity was decreased by 70% or more by heat treatment for the first 2 minutes, and the activity was decreased by 90% or more from 5 minutes. This result indicates that the thermal sensitivity of the mutant UDG of the present disclosure was significantly higher than that of the wild type.

Example 5. Tm Analysis of the Mutant UDG Compared to Wild Type

Figure 8:
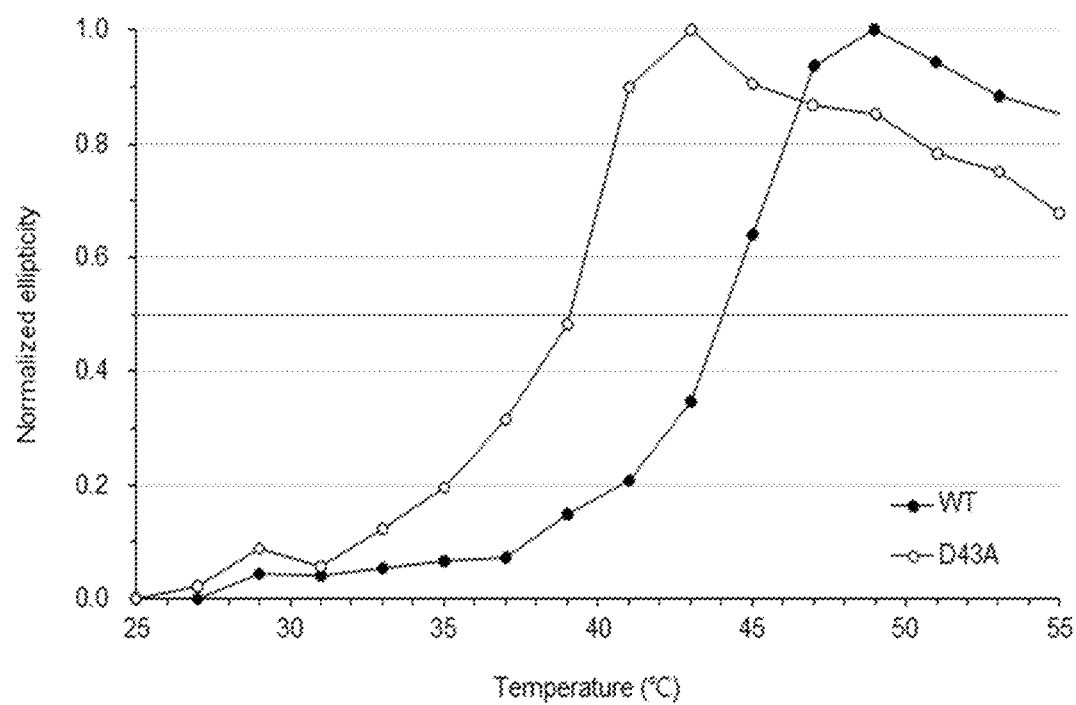
FIG. 8 is the result of CD (circular dichroism) analysis using J-815 CD spectrometer (Jasco, Japan) to measure the differences of mutant D43A and wild-type UDG. Based on the results, it is determined that Tm of WT UDG is about 44° C. and Tm of D43A is about 39° C. The results show that the 3D structural stability of the mutant D43A UDG is lower than that of the wild-type UDG, supporting the high thermal sensitivity of the mutant UDG.

Using the proteins purified in Example 4, the melting temperatures of the wild-type and D43A mutant UDGs were analyzed. To this end, Circular dichroism (CD) analysis was performed using a J-815 CD spectrometer (Jasco, Japan) according to the manufacturer's instruction. The ellipticity at 222 nm was measured in units of 2° C. while increasing the temperature from 25° C. to 95° C. The results are shown in FIG. 8. As shown therein, the Tm of the WT was measured to be about 44° C. and the Tm of the D43A mutant was about 39° C., indicating that the Tm of the mutant UDG was about 5° C. lower than that of the wild-type. This result indicates that the D43A mutant has a lower three-dimensional structural stability than that of the wild type, and thus supports the high thermal sensitivity of the present mutant.

Figure 9:
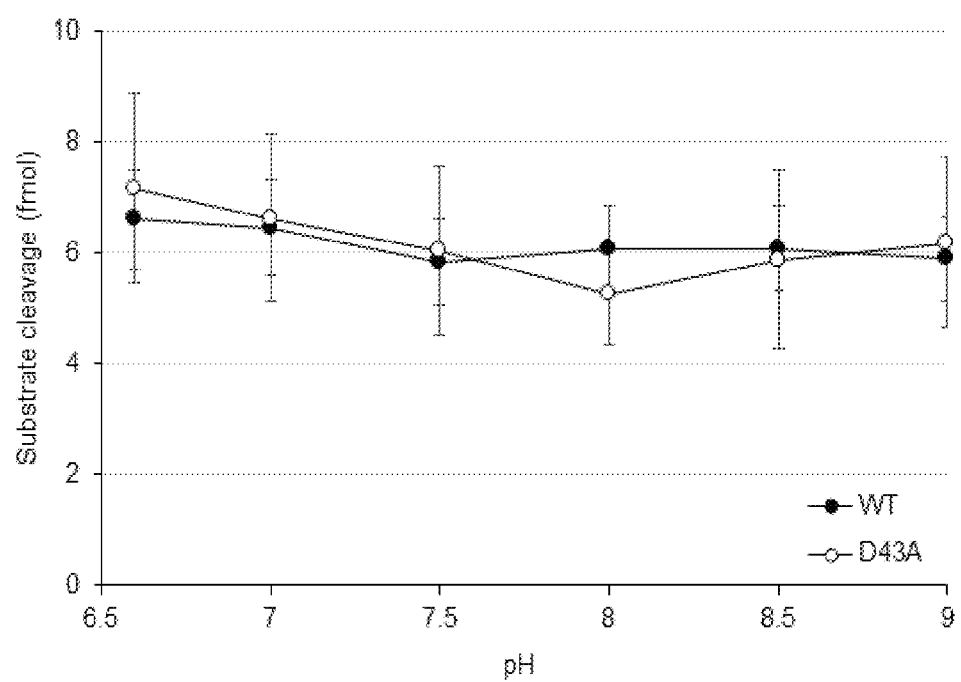
FIG. 9 is the result of the experiments to measure various biochemical characteristics of the mutant UDGs and wild-type UDG in various buffer conditions. The changes in the activity of UDGs were measured by varying the pH from 6.6 to 9. The results show that it does not have a significant effect on the enzyme activity of D43A and the wild-type UDG.

Example 6. Analysis of the Activity in Various pH, Salt, and Divalent Cation Concentrations in the Mutant UDGs Compared to Wild Type Using the proteins purified in Example 4, various biochemical properties of wild-type and D43A mutant UDG were measured under various buffer conditions. First, as a result of measuring the changes in the activity of UDG by varying the pH from 6.6 to 9, it was confirmed that neither the D43A mutant nor the wild type was significantly affected in their enzyme activities (see FIG. 9).

Figure 10:
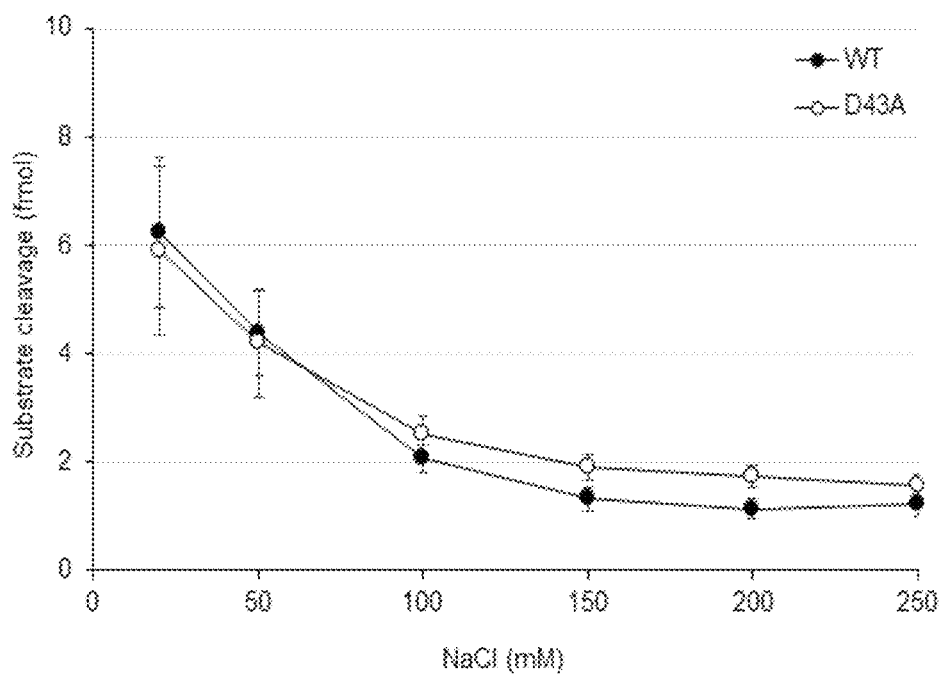
FIG. 10 is the result of measuring the activity of mutant and wild-type UDG by varying the NaCl concentrations from 20 to 250 mM in order to evaluate the effect of the salt concentration on the activity of the mutant and wild-type UDG. It was found that both mutant and wild-type UDG showed high activity at low salt concentration, and the higher the salt concentration was, the more it inhibited the activity. In particular, it was found that only about 20% of the UDG activity was remained at 200 mM or more in comparison to that of at 20 mM, and it was confirmed that the inhibitory effect on the activity by the salt concentration was similar in both wild type and mutant UDG.

In order to evaluate the effect on the activity according to the salt concentrations, the activity was measured by varying the NaCl concentration from 20 to 250 mM. Both wild-type and mutant UDG showed high activity at low salt concentration, and it was confirmed that the activity was inhibited as the salt concentration increased. In particular, it was found that at the salt concentration of 200 mM or more, only about 20% of the UDG activity shown at 20 mM was remained, and it was confirmed that the inhibitory effect on the activity by the salt was similar for both wild-type and mutant (see FIG. 10).

Figure 11:
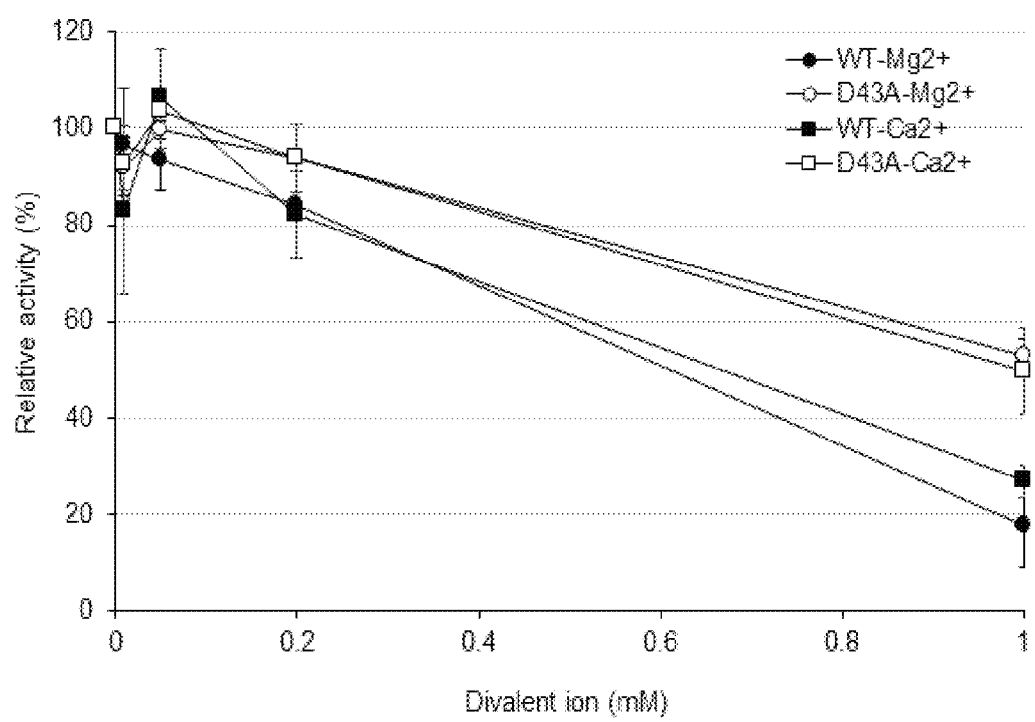
FIG. 11 is the result of measuring the enzymatic activity changes of the mutant UDG and wild-type UDG according to the concentration of the divalent metal ions. For this, $MgCl_2$, $CaCl_2$), $ZnCl_2$, CoCl2, and $MnCl_2$ were used in various concentrations from 0.01 to 1 mM. As a result of the experiment, it was found that in both wild-type and mutant UDG, the activity was almost inhibited as the concentration of divalent metal ions increased. There was little difference in the degree of inhibition of the activity between the mutant and wild-type UDG according to the concentration of divalent metal ions.
Figure 12:
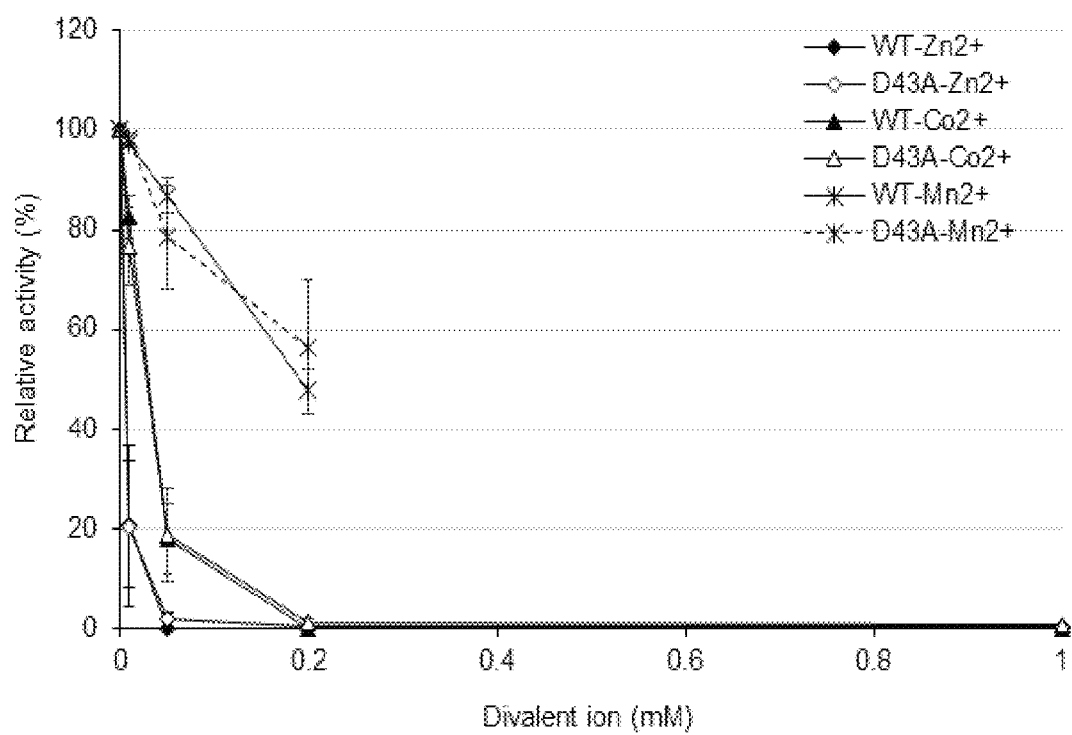
FIG. 12 is the result of measuring the enzymatic activity changes according to the concentration of $ZnCl_2$ and $CoCl_2$ in mutant and wild-type UDGs. It was found that in the case of $ZnCl_2$ and $CoCl_2$, at least 95% of the enzymatic activity was inhibited at 0.05 mM and 0.2 mM, respectively.

Finally, the change of enzyme activity according to the concentration of divalent metal ions was measured. For divalent metal ions, $MgCl_2$, $CaCl_2$, $ZnCl_2$, $CoCl_2$, and $MnCl_2$ were used in various concentrations from 0.01 to 1 mM. As a result of the experiment, it was confirmed that the activity of both wild-type and mutant UDG was inhibited as the concentration of divalent metal ion increased (see FIGS. 11 and 12). In particular, in the case of $ZnCl_2$ and $CoCl_2$, it was confirmed that at least 95% of the enzyme activity was inhibited at 0.05 mM and 0.2 mM, respectively (FIG. 12). However, it was confirmed that there was little difference in the degree of inhibition in the activity according to the concentration of divalent metal ions between the mutant and wild type UDGs.

Example 7. Analysis of Optimal Reaction Temperature of the Mutant UDG

Figure 13:
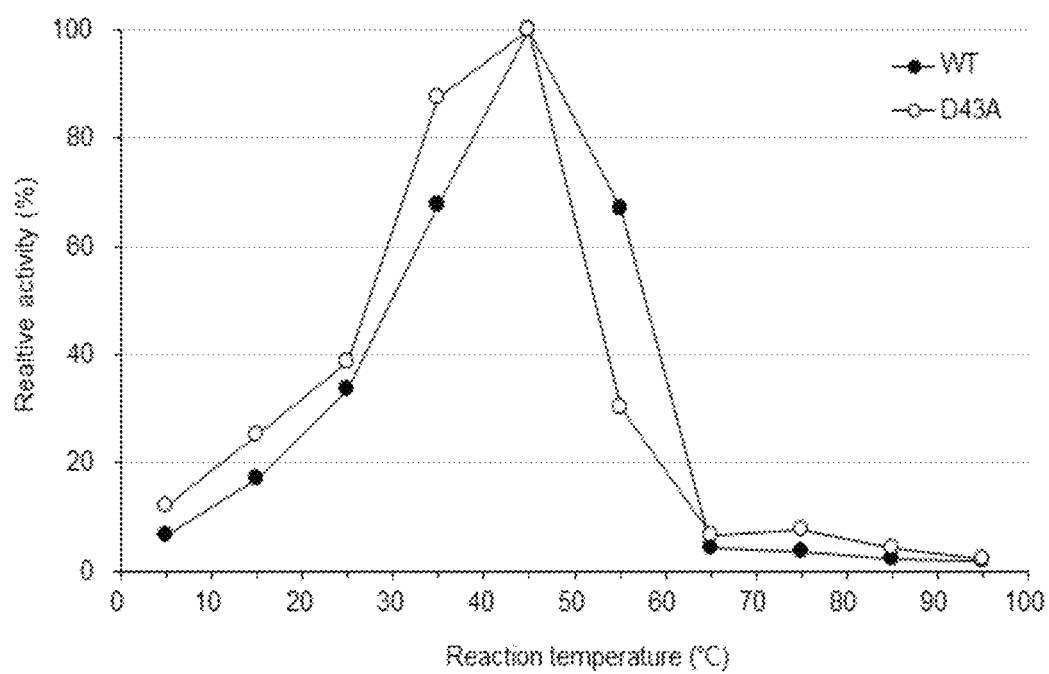
FIG. 13 is the result of measuring the enzymatic activity at 5° C. intervals from 5 to 95° C. to confirm the optimal reaction temperature of the wild type and mutant UDGs. As a result of the experiment, it was confirmed that both wild-type and mutant showed optimal activity at 45° C. However, in the case of D43A mutant, which is confirmed to be highly sensitive to heat, the activity at 35° C. was measured about 3 times higher than the activity at 55° C. (in case of wild-type UDG, the activity was almost similar at both temperatures), indicating that the overall optimal temperature for the activity is shifted toward a lower side in D43A UDG compared to that of wild type UDG. This result is judged to be due to the high heat sensitivity of the D43A mutant compared to the wild type UDG.

Using the proteins purified in Example 4, the optimal reaction temperature of the wild-type and D43A mutant UDGs was analyzed. For this, the enzyme activity was measured at 5° C. intervals from 5 to 95° C. The results are shown in FIG. 13. As a result of the experiment, it was confirmed that both wild-type and mutant showed optimal activity at 45° C. However, in the case of the D43A mutant, which was confirmed to be highly sensitive to heat, the activity at 35° C. was measured about 3 times lower than that at 55° C. (in case of the wild type, the activities were nearly identical at both temperatures), this indicates that the optimal temperature of the mutant UDG is toward at the lower side compared to that of the wild-type UDG (FIG. 13). This result is judged to be due to the high thermal sensitivity of the D43A mutant compared to the wild type.

Example 8. Experiment to Prove that the Inhibitory Effect on PCR by the Unconventional UDG is Reduced by the Mutant UDG in Real-Time PCR It is known that the most widely used *E. coli*-derived UDG, when applied to real-time PCR, is not completely inactivated during the PCR process, and thus it is observed that there is a side effect of reducing the efficiency of real-time PCR by partially decomposing the PCR amplification products.

In the case of the heat-sensitive UDG mutants developed herein, it was thought that there would be no such side effects as they were rapidly inactivated during the PCR process. In order to prove this experimentally, the following experiment was performed. GAPDH gene was used as a target. In order to amplify the GAPDH target using 10 ng of human cDNA as a template, Forward (5'-ACGGAT-TTGGTCGTATTGGGC-3') (SEQ ID NO: 157), Reverse (5'-TTGACGGTGCCATGGAATTTG-3') (SEQ ID NO: 158) primers and A fluorescent TaqMan® probe (5' FAM-CCTGGTCACCAGGGCTGCTTTTAA-TAMRA 3') (SEQ ID NO: 159) were used (Genotech, Korea). For the gene amplification, 1 unit (50 ng/unit) of wild-type Taq polymerase and 0, 1, 2, 5, or 10 ng of wild-type or mutant UDGs were added to a standard PCR buffer (10 mM Tris-HCl/pH 8.3, 1.5 $MgCl_2$, 50 mM KCl, 0.2 mM dNTP). The PCR reaction was performed using real-time PCR equipment (CFX96™, Bio-Rad) as follows: a 4 minute-UDG reaction step at 50° C., a 15-minute pre-denaturation step at 95° C., and a total of 50 cycles with one cycle of 95° C. for 10 seconds, 50° C. for 40 seconds, and 60° C. for 20 seconds. A total of 50 cycles were performed with 20 seconds. Then relative fluorescence values were measured and shown at each cycle after the step at 50° C. for 40 seconds.

Figure 14:
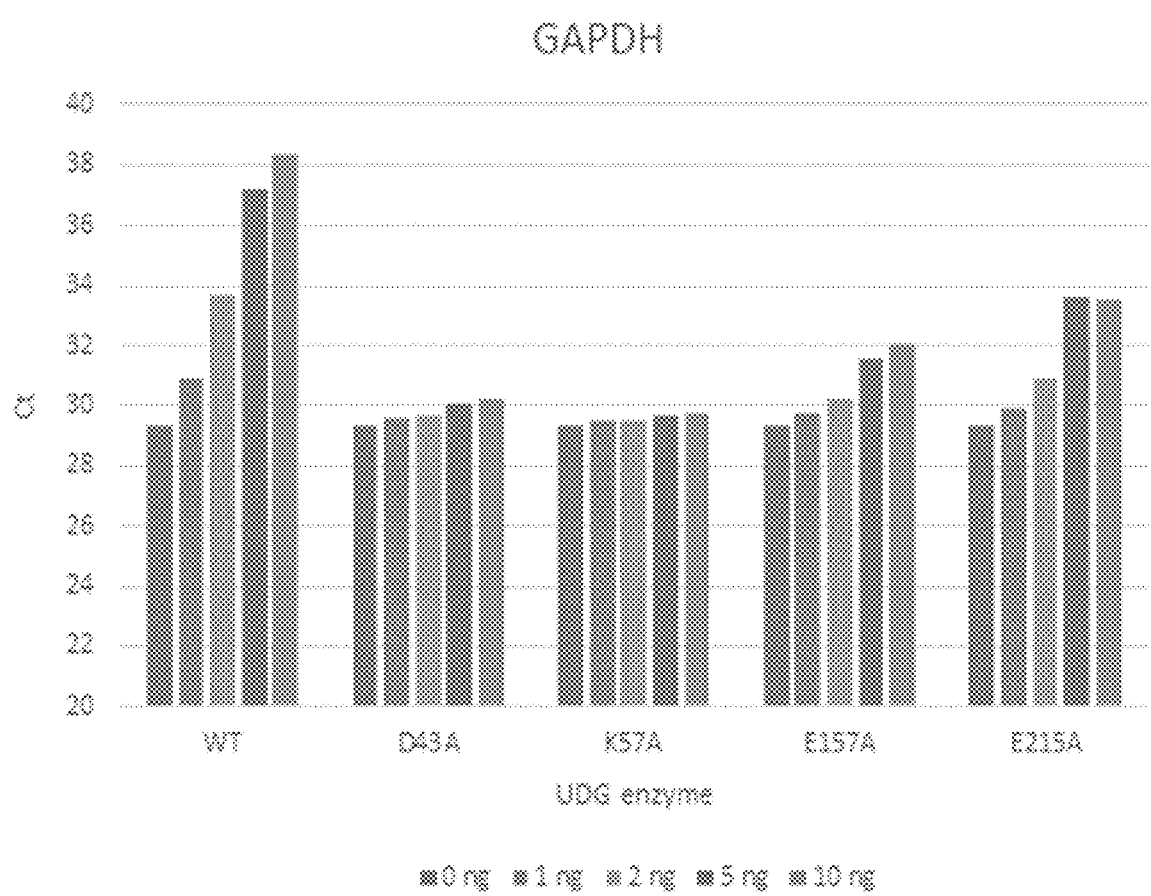
FIG. 14 is the result of measuring the inhibitory effect of the mutant and wild-type UDGs on PCR efficiency in Real-Time PCR. When the wild-type UDG was used, the Ct (Cycle threshold) value was increased in proportion to the amount of UDG added to the reaction. This indicates that the wild-type UDG is not completely inactivated in the pre-denaturation step following the UDG reaction step, and thus the amplified products in the subsequent PCR amplification steps are degraded. However, it was confirmed that the mutant UDG of the present application showed higher heat sensitivity compared to the wild type, and in particular, the D43A and K57A mutants were rapidly inactivated under the 95° C. reaction conditions during the PCR process, and there was little change in the Ct value depending on the amount of UDG added.

The results are shown in FIG. 14. As shown therein, when the wild-type UDG was used, it was confirmed that the Ct (Cycle at threshold) value was increased in proportion to the amount of UDG added to the reaction. This means that the wild-type UDG is not completely inactivated in the pre-denaturation step after the UDG reaction process, and thus the amplified products generated in the subsequent PCR amplification reaction were degraded. However, in the case of the present D43A and K57A mutant UDGs, it was confirmed that there were little changes in the Ct values depending on the amount of UDG added because they were completely and rapidly inactivated during the pre-denaturation step at 95° C. during the PCR reaction. It was also confirmed that the E157A and E215A mutants showed a Ct value increase lower than that of the wild type, indicating the higher thermal sensitivity compared to the wild type UDG.

Example 9. Preparation of the Mutants Having Various Substitutions at Position 43 Other than Alanine and Analysis of Thermal Sensitivity Thereof In order to find mutations with a more improved thermal sensitivity, experiments were performed to change the selected residues into various amino acids. To this end, various enzymes with high structural similarity to *E. coli*

UDG were subjected to free energy calculation using molecular dynamics simulation, multiple sequence alignment, and stability analysis using a commercial web server. Through this process, eight amino acid substitutions at D43 residue that were calculated as those that mostly reduces the thermal stability. These were C, G, K, H, I, P, R, V, and W, respectively. The mutant UDGs were constructed by site-directed mutagenesis, cloned and expressed and purified as in Examples 2 and 3, The primer sets used for this is listed in Table 3.

Figure 15:
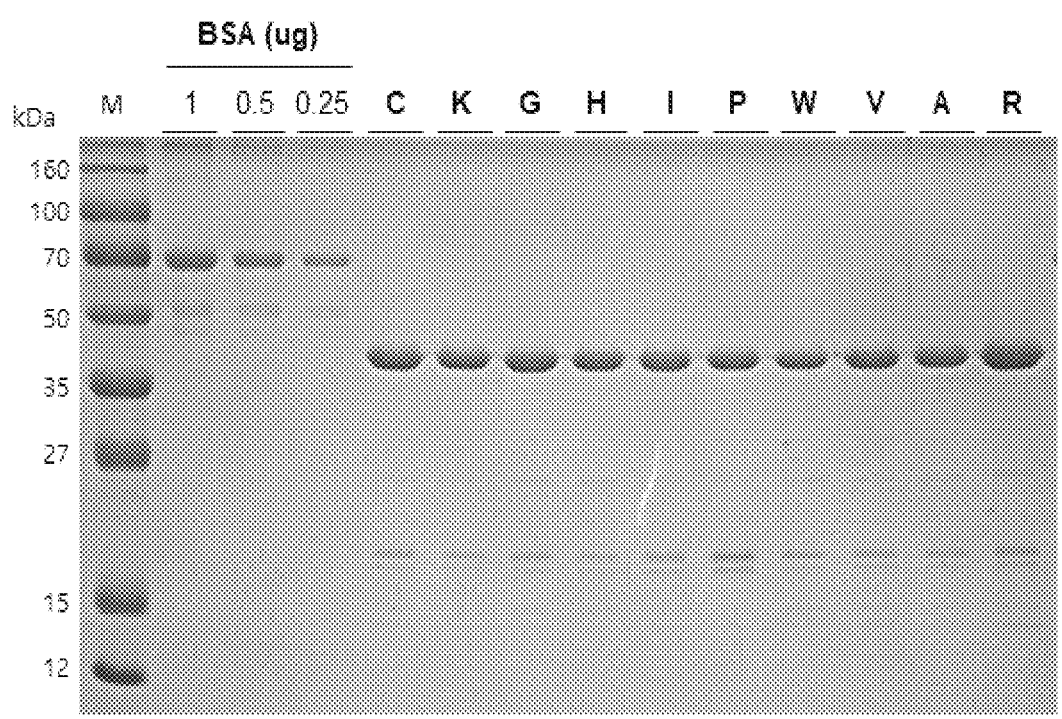
FIG. 15 is the result of expression and purification of the mutant UDGs in which D43 position is substituted with amino acid C, G, K, H, I, P, R, V, or W according to one embodiment of the present invention. The results of the in vitro UDG activity assay for the mutation are described in FIGS. 16 and 17.

The results of expressing these mutant UDGs are shown in FIG. 15.

Figure 16:
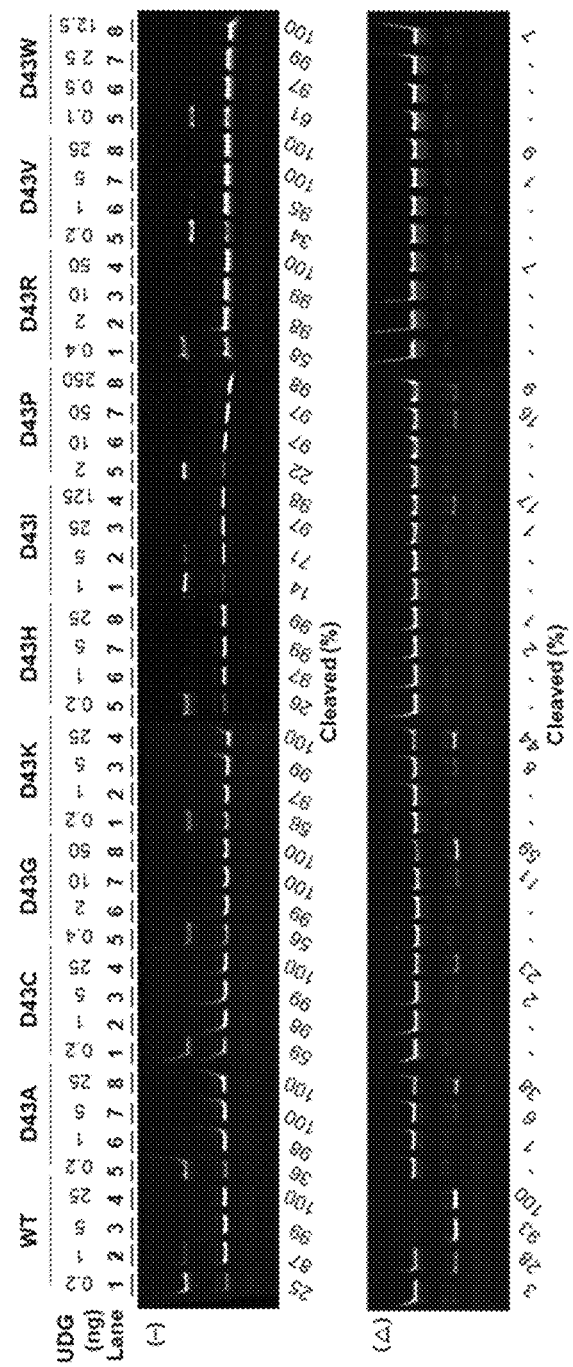
FIG. 16 is the result of analyzing the thermal sensitivity of the mutant UDGs prepared in FIG. 15 by in vitro UDG activity assay. When the D43 position was changed to each of H, R, V, and W, the heat sensitivity was increased by 53, 52, 32 and 65 times respectively compared to the wild type. In the case of D43A, the thermal sensitivity increased by about 8 times which is similar to the above experiment results. The remaining C, G, K, I, and P mutations also showed an increase in the heat sensitivity although there are some differences, but the heat sensitivity increased by about 3 to 15 times compared to that of the wild type.
Figure 17:
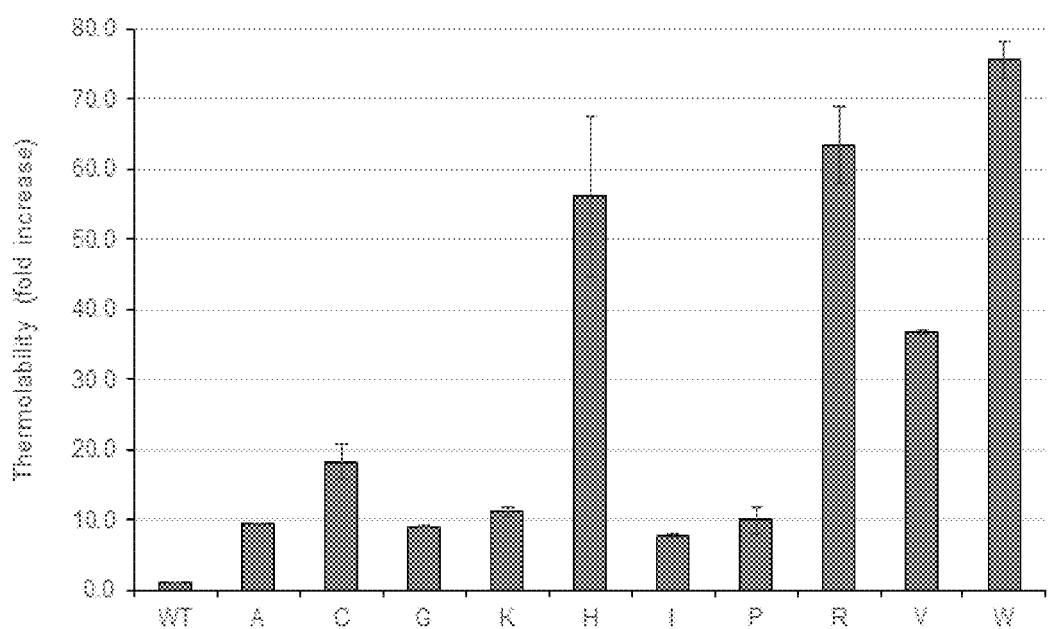
FIG. 17 shows the results of FIG. 16 as a multiple of the increase in the heat sensitivity compared to that of the wild type.

The results of the in vitro UDG activity assay using these mutants are shown in FIGS. 16 and 17. As a result of the experiments, when the D43 position was changed to H, R, V, and W, respectively, it was found that the thermal sensitivity was increased by 53, 52, 32 and 65 times compared to that of wild type, respectively. In the case of D43A, it was confirmed that the thermal sensitivity was increased by about 8 times compared to that of wild type, which is similar to the above experiment results. The remaining C, G, K, I, and P mutants were shown to be increased in thermal sensitivity about 3 to 15 times compared to the wild type. Through these results, it was confirmed that even when an amino acid other than A was introduced at the D43 position, the thermal sensitivity is increased compared to that of the wild type. In particular, in case of H, R, V, W mutants, the thermal sensitivity was increased 4 to 8 times more than that of the wild type.

Figure 18:
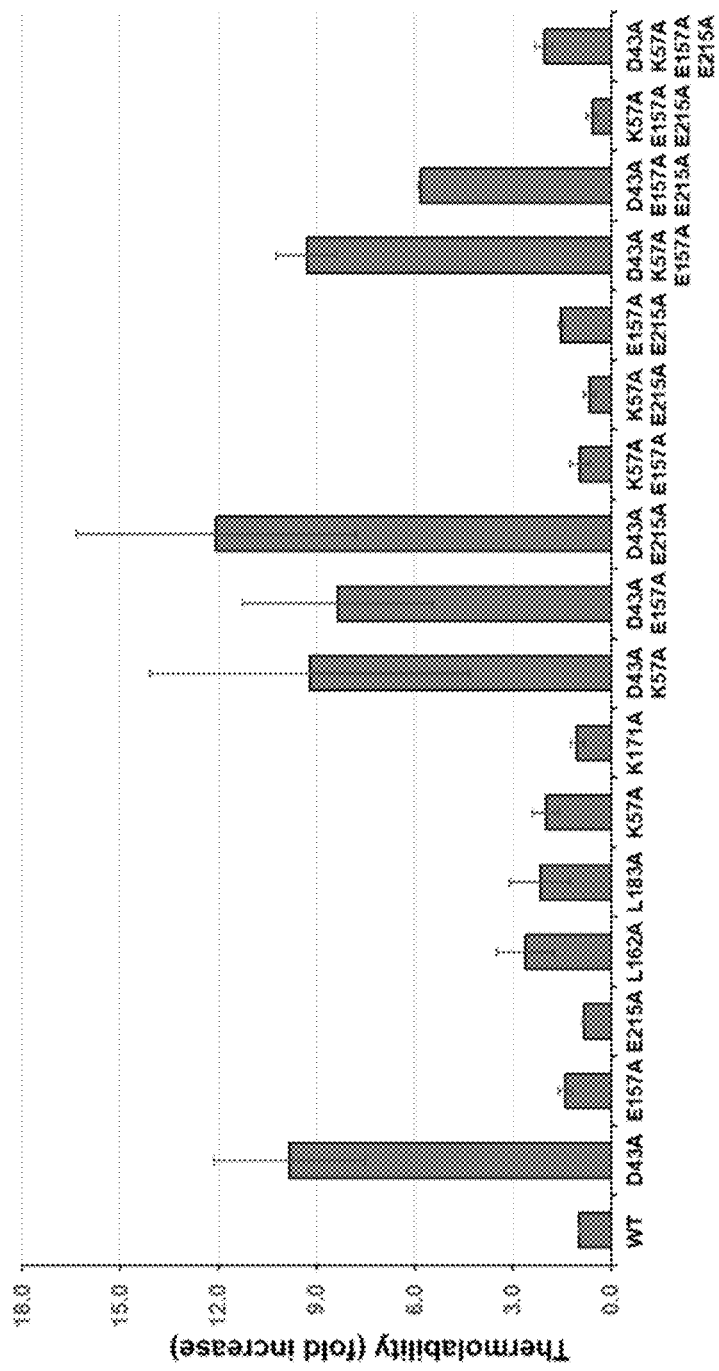
FIG. 18 is the result of measuring the thermal sensitivity of the UDG containing two or more mutations selected from the D43A, E157A, E215A, L162A, L183A, K57A and K171A. It was confirmed that all of the D43A/K57A, D43A/E157A, D43A/E215A, D43A/K57A/E157A, D43A/E157A/E215A, D43A/K57A/E157A/E215A mutations exhibited the increased heat sensitivity more than twice that of the wild type. However, in the case of the combination mutations not containing D43A, the effect of increasing the heat sensitivity was within 1.5 times. These results indicate that the mutation at D43 position is important in determining the thermal stability of *E. coli* UDG.

Example 10. Preparation of the Combination Mutants and Analysis of Thermal Sensitivity Thereof Next, the combination mutations were constructed to confirm whether thermal sensitivity was further increased when the mutations identified above are combined with each other. Single, double, triple, and quadruple mutations were constructed by combining the first selected amino acid residues, and the new candidate mutations were further combined and in vitro UDG activity assays were performed for a total of 17 mutant UDGs. The results are shown in FIG. 18. Based on the results of the assay, the mutants combined with D43A mutation that is: D43A/K57A, D43A/E157A, D43A/E215A, D43A/K57A/E157A, D43A/E157A/E215A, D43A/K57A/E157A/E215A showed the thermal sensitivity increased at least 2 times in comparison to the wild-type. In contrast, in the case of the combination mutations not containing D43A, it was confirmed that the increase in the thermal sensitivity was within 1.5 times in comparison to wild-type. Taking these results together, it was confirmed that the mutation at the D43 position plays an important role in determining the thermal stability of *E. coli* UDG.

Example 11. Construction of Various Mutant UDGs and Analysis of Thermal Sensitivity Thereof In order to screen a wider variety of thermal sensitive UDGs, the mutant UDGs were constructed by substituting the residues of E4, W7, Y19, F48, E52, H67, Q71, H73, F77, R80, P87, L96, E112, L121, F144, F161, G214 of wild-type UDG with alanine, glutamic acid, arginine or tryptophan. The substituted residues were selected by free energy calculation based on the structure similar to the previous Examples.

Figure 19:
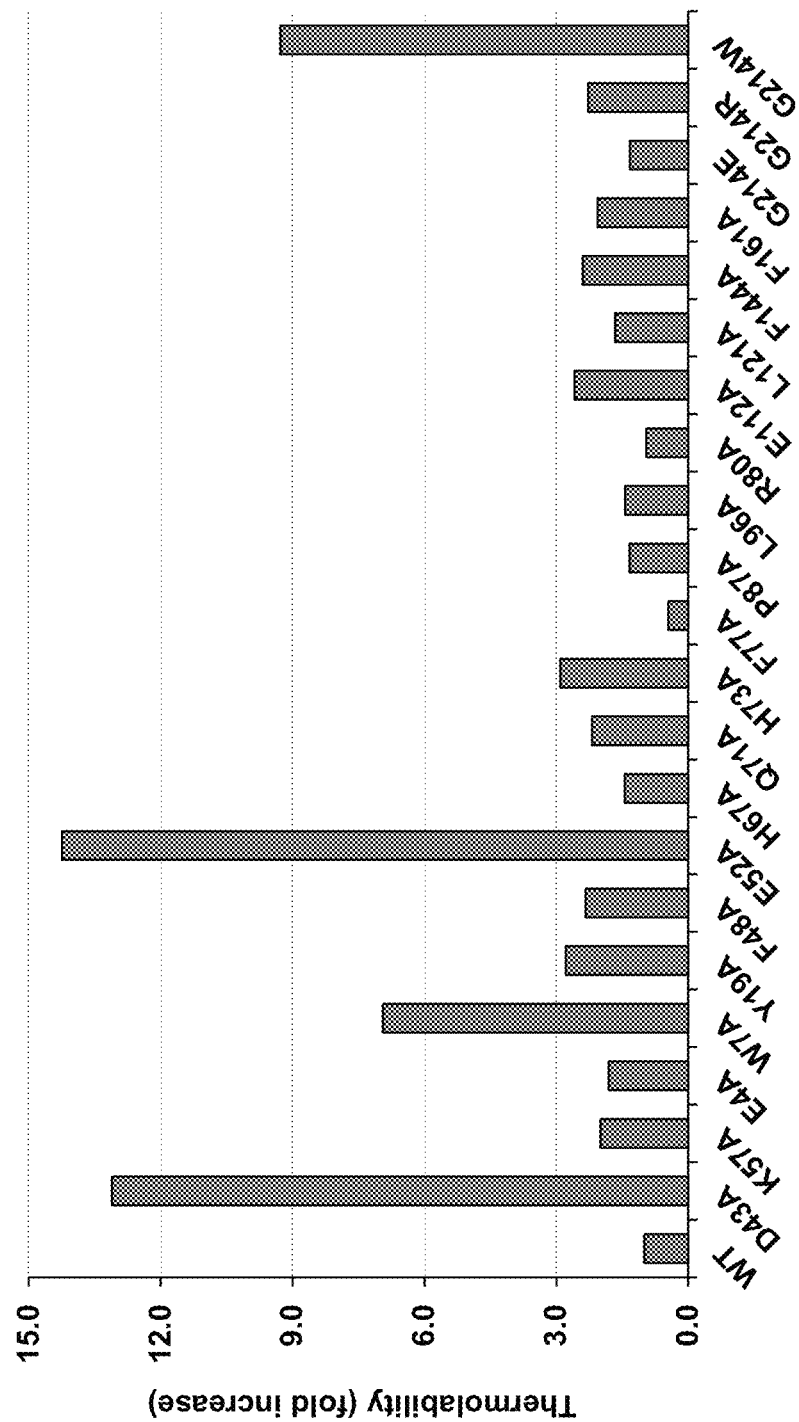
FIG. 19 is the results of measuring the thermal sensitivity of a total of 19 different kinds of mutants in which E4, W7, Y19, F48, E52, H67, Q71, H73, F77, R80, P87, L96, E112, L121, F144, F161, and G214 residues were substituted with glutamic acid, arginine, ortryptophane. In the case of W7A, E52A, and G214W mutant enzymes, it was confirmed that heat sensitivity was increased by 6.9 times, 14.2 times, and 9.3 times, respectively, compared to the wild type UDG. In addition, Y19A, F48A, Q71A, H73A, E112A, F144A, F161A, and G214R mutants also showed the heat sensitivity increased at least two times compared to the wild type UDG.

The results are shown in FIG. 19. As shown therein, as a result of comparing and measuring the thermal sensitivity of a total of 19 purified mutant UDGs with the D43A mutant, the thermal sensitivity of W7A, E52A, and G214W mutant enzymes increased 6.9 times, 14.2 times, and 9.3 times, respectively, in comparison to that of wild type. In addition, in the case of Y19A, F48A, Q71A, H73A, E112A, F144A, F161A, and G214R mutations, it was confirmed that the thermal sensitivity increased by about 2 times or more.

Example 12. Analysis of Inactivation Temperature of the Present Mutant UDGs and Wild-Type UDG and Whether they are Reactivated after the Inactivation Among the mutant UDGs according to the present application, the comparative experiments were performed on D43A, D43C, D43H, D43R, D43V, and D43W mutants.

The concentration of wild-type UDG and the present UDGs to cleave the same amount of the substrate was determined in the preliminary experiment. That amount of the mutant UDGs and wild-type UDG was then heat treated for 5 minutes by varying the temperature from 35° C. to 95° C. at 10° C. intervals followed by 15 min reaction at 35° C. to measure the activity of UDGs.

Figure 20:
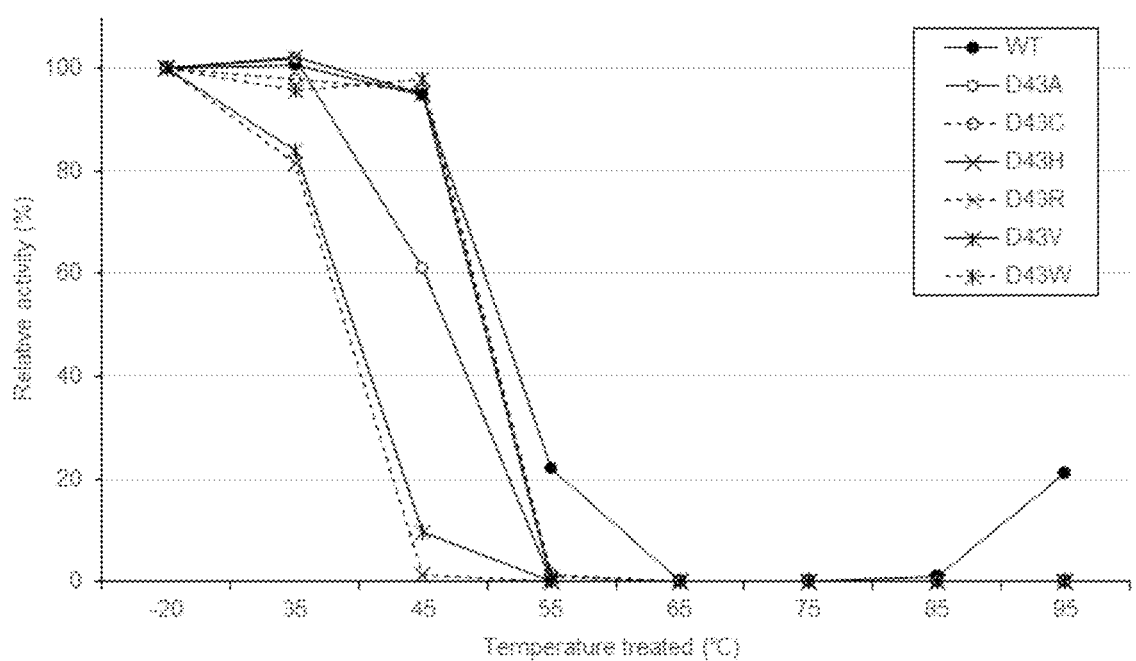
FIG. 20 is the result of measuring the thermal sensitivity and the reactivation after the inactivation of the D43A D43C, D43H, D43R, D43V, D43W UDGs of the present invention and wild-type UDG. In the case of wild-type UDG, it was confirmed to retain 22% of the activity even after heat treatment at 55° C., but it was confirmed that the UDGs according to the present application were inactivated by 90% or more at 45° C. Furthermore, in the case of wild-type UDG, it seemed completely inactivated at 65° C. and 75° C., but it was found that some activity was still remained and reactivated at 85° C. and 95° C., but the UDGs according to the present application did not show such phenomenon. This indicates that the UDGs of the present disclosure are most effectively inactivated and not reactivated due to their high thermal sensitivity, and thus does not inhibit with the subsequent reactions such as RT and PCR, so that the present UDGs can be advantageously used with RT or PCR without sacrificing the efficiency thereof.

The results are shown in FIG. 20. As shown there, it was confirmed that all the mutant UDGs were inactivated at 55° C. or more. In the case of wild-type UDG, it was confirmed to retain 22% of the activity even after the heat treatment at 55° C., whereas in the case of D43A, D43C, D43H, D43R, D43V, and D43W of the present disclosure, it was confirmed that they were completely inactivated at the corresponding temperature, indicating the high thermal sensitivity of the present mutant UDGs.

In addition, it was confirmed that inactivation of D43A mutant started from 45° C., and D43R and D43V mutants started from 35° C., indicating that the thermal sensitivity thereof is considerably high. This also indicates that the inactivation of the present mutant UDGs starts at the temperature lower than the temperature of RT (Reverse Transcription) reaction which is 42° C., and thus do not inhibit the RT reaction.

In addition, wild-type UDG was completely inactivated at 65° C. and 75° C., but it was confirmed that it was reactivated after heat treatment at 85° C. and 95° C., the mechanism of which has not been elucidated. But the mutant UDGs according to the present disclosure did not show any reactivation.

This indicates that D43A, D43C, D43H, D43R, D43V, and D43W of the present disclosure are effectively inactivated and not reactivated due to their high thermal sensitivity, so when used in PCR reactions, they do not inhibit PCR, indicating that the efficiency of PCR can be most effectively increased.

While this disclosure has been described in connection with what is presently considered to be practical exemplary embodiments, it is to be understood that the disclosure is not limited to the disclosed embodiments, but, on the contrary, is intended to cover various modifications and equivalent arrangements included within the spirit and scope of the appended claims.

Unless defined otherwise, all technical and scientific terms and any acronyms used herein have the same meanings as commonly understood by one of ordinary skill in the art in the field of the invention. The contents of all publications disclosed as references herein are incorporated herein by reference.

What is claimed is:

1. An isolated UDG (Uracil DNA Glycosylase) polypeptide from *Escherichia coli* consisting of the amino acid sequence set forth in SEQ ID NO: 1 having at least one amino acid substitution selected from the group consisting of E4A, W7A, E13A, Q16A, Y19A, D43X, F48A, F50A, E52A, H67A, K57A, Q71A, H73A, P87A, L96A, E112A, L121A, H134A, E142A, F144A, R156A, F161A, L162A, W164A, H180A, L183A, H202A, G214E, G214W, G214R, W220A, and L224A, in which the number indicates the position of the substituted amino acid and the amino acids are indicated as a single letter code and X indicates any amino acids, in which the codes on the left and right sides of the position indicate a wild type and substituted residues, respectively, wherein the UDG has an improved thermal sensitivity in comparison to a wild type UDG from *E. coli*, wherein the X of D43X is A, C, G, K, H, I, P, R, V or W.

2. The isolated UDG of claim 1, wherein the UDG polypeptide comprises at least one substitution selected from the group consisting of D43A, D43C, D43H, D43R, D43V, D43W and K57A.

3. The isolated UDG of claim 1, wherein the UDG polypeptide further comprises E157A or E215A substitution.

4. The isolated UDG of claim 1, wherein the UDG polypeptide comprises a combination of at least two substations-substitutions and is selected from the group consisting of D43A/K57A, D43A/E157A, D43A/E215A, D43A/K57A/E157A, D43A/E157A/E215A, and D43A/K57A/E157A/E215A.

5. A kit for removing nucleic acid contaminants in RT (Reverse Transcription), PCR (Polymerase Chain Reaction) or RT-PCR or RT-PCR reaction mixture, comprising the UDG polypeptide according to claim 1.

6. A premix composition for PCR comprising the UDG polypeptide according to claim 1, a PCR polymerase and a buffer necessary for a PCR reaction.

7. A premix composition for RT comprising the UDG polypeptide according to claim 1, a reverse transcriptase and a buffer necessary for a RT reaction.

8. A premix composition for RT-PCR comprising the UDG polypeptide according to claim 1, a PCR polymerase, a reverse transcriptase and a buffer necessary for a RT-PCR reaction.

9. A nucleic acid encoding the UDG polypeptide according to claim 1.

10. A vector comprising the nucleic acid of claim 9.

11. A prokaryotic cell comprising the vector of claim 10.

\* \* \* \* \*